US011249023B2

(12) United States Patent
He et al.

(10) Patent No.: US 11,249,023 B2
(45) Date of Patent: Feb. 15, 2022

(54) RAPID DETECTION METHOD FOR CONDITION OF LANDFILL LEACHATE POLLUTING GROUNDWATER AND APPLICATION THEREOF

(71) Applicant: Chinese Research Academy of Environmental Sciences, Beijing (CN)

(72) Inventors: Xiaosong He, Beijing (CN); Mingxia Zheng, Beijing (CN); Beidou Xi, Beijing (CN); Guangchun Shan, Beijing (CN); Jing Su, Beijing (CN); Xuemei Fu, Beijing (CN); Yuanyuan Sun, Beijing (CN); Hongyu Ding, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 5 days.

(21) Appl. No.: 16/907,446

(22) Filed: Jun. 22, 2020

(65) Prior Publication Data
US 2020/0348232 A1 Nov. 5, 2020

(30) Foreign Application Priority Data
Apr. 28, 2020 (CN) .......................... 202010351038.9

(51) Int. Cl.
*G01N 21/64* (2006.01)
*G01N 33/18* (2006.01)
*G01N 21/94* (2006.01)

(52) U.S. Cl.
CPC ......... *G01N 21/6428* (2013.01); *G01N 21/94* (2013.01); *G01N 33/18* (2013.01);
(Continued)

(58) Field of Classification Search
CPC .... G01N 21/6428; G01N 21/94; G01N 33/18; G01N 33/1826; G01N 2021/6419; G01N 2021/6421; G01N 21/6486
See application file for complete search history.

(56) References Cited

U.S. PATENT DOCUMENTS
2007/0090059 A1* 4/2007 Plummer ................ C02F 1/008
210/743

FOREIGN PATENT DOCUMENTS
CN 102890075 A * 1/2013
CN 102901721 A * 1/2013

OTHER PUBLICATIONS

Baker et al., "Fluorescence of leachates from three contrasting landfills", 2004, Water Research, 38, 2605-2613 (Year: 2004).*
(Continued)

*Primary Examiner* — Samuel P Siefke
*Assistant Examiner* — Henry H Nguyen
(74) *Attorney, Agent, or Firm* — Duane Morris LLP

(57) ABSTRACT

Provided are a rapid detection method for a condition of landfill leachate polluting groundwater and an application thereof. The rapid detection method includes: carrying out fluorescence detection on groundwater in a specific region of a landfill, and determining whether the groundwater is polluted according to a ratio of fluorescence intensities at specific excitation/emission wavelengths in a specific fluorescence region. The rapid detection method provided by the solution establishes characteristic fluorescence spectrum regions, fluorescence intensities and regular characteristics thereof of organic matters in leachate-polluted groundwater of a landfill in a fluorescence spectrum region, and can achieve the rapid detection of a condition of landfill leachate polluting groundwater by means of a portable fluorescence detector on site. The detection method provided by the solution is characterized by rapid detection, no need of (Continued)

chemical reagents, simple operation, high detection sensitivity and lower cost.

10 Claims, 13 Drawing Sheets

(52) U.S. Cl.
CPC .  *G01N 33/1826* (2013.01); *G01N 2021/6419* (2013.01); *G01N 2021/6421* (2013.01)

(56) References Cited

OTHER PUBLICATIONS

Pan et al., "Assessment on the leakage hazard of landfill leachate using three-dimensional excitation-emission fluorescence and parallel factor analysis method", Jun. 2017, Waste Management, 214-221 (Year: 2017).*
Ngoc et al., "Heavy metal speciation in landfill leachate and its association with organic matter", 2019, IOP Conf. Series: Earth and Environmental Science, 266, 012006 (Year: 2019).*
U.S. Environmental Protection Agency, "RCRA Ground-Water Monitoring: Draft Technical Guidance", Nov. 1992, Office of Solid Waste, U.S. Environmental Protection Agency (Year: 1992).*
Translation of CN102901721A, Xi, Bei-dou, Jan. 30, 2013 (Year: 2013).*
Translation of CN102890075A, He, Xiao-song, Jan. 23, 2013 (Year: 2013).*

* cited by examiner

_US 11,249,023 B2_

RAPID DETECTION METHOD FOR CONDITION OF LANDFILL LEACHATE POLLUTING GROUNDWATER AND APPLICATION THEREOF

CROSS-REFERENCE TO RELATED APPLICATIONS

This application claims priority to Chinese Patent Application No. 202010351038.9, filed on Apr. 28, 2020, the contents of which are incorporated herein in its entirety by reference.

TECHNICAL FIELD

The present invention belongs to the field of environment monitoring, and relates to a rapid detection method for a condition of landfill leachate polluting groundwater and an application thereof.

BACKGROUND

Landfill poses the greatest potential for groundwater pollution, since the landfill can produce a large amount of leachate containing various high-concentration pollutants, which is prone to leaking and polluting the groundwater. At present, the monitoring of groundwater is mainly performed by means of on-line monitoring and laboratory test with manual sampling. The laboratory test has the disadvantages of tedious procedures and time consuming. The on-line monitoring system has the defects of high price and high maintenance cost, and can only monitor some simple indexes such as conductivity, ammonia nitrogen and Pondus Hydrogenii (pH), and some complex indexes cannot be monitored through the on-line monitoring system. However, the landfill leachate has high contents of diverse organic pollutants. Therefore, the rapid and efficient detection of the organic matters in the groundwater near the landfill is an effective way for identifying the groundwater pollution caused by the landfill.

The composition and structure of the organic matter are analyzed mainly adopting conventional index analysis, spectral technology and chromatographic technology. Unlike the spectral detection technology, the conventional index analysis and chromatographic detection involve complex sample pretreatment and require chemical agents which easily produces pollutants. Compared with the conventional index analysis and chromatographic detection, the spectral detection technology has the advantages of no need of chemical reagents, no damage to the structure of a sample, and measurement rapidity and flexibility. The leachate contains a large amount of benzene pollutants which are monocyclic and polycyclic aromatic hydrocarbons, and has strong spectral characteristics, particularly fluorescence and ultraviolet characteristics, so that the ultraviolet and fluorescence spectra are characterized by simple, convenient and rapid detection in composition analysis of organic matters. Yigang Xu, et al. (Yigang Xu, Qing Li, Yi Wu, et al. Remote groundwater chemical oxygen demand (COD) on-line detector design, _Computer Measurement and Control_, 2017 (11): 316-320) establishes a relation between the absorbance of the organic matters in the ultraviolet light spectral region and the COD concentration by using the characteristic that organic matters have strong absorption at a specific ultraviolet light wavelength, and designs a COD on-line detector for remote groundwater. However, the detector is suitable for the water with lower groundwater turbidity and needs manual addition of clean water periodically in a cleaning mode, and thus has the defect of inconvenient operation. At present, the route for monitoring water quality using the fluorescence spectrum at home and abroad is mostly to obtain a three-dimensional fluorescence spectrum, and further analyze the spectrum (For example, Yun Zhou, Jun Li, Fei Chen, et al. Study on the 3D fluorescence feature of styrene and emergent treatment of styrene pollutant in water, _Spectroscopy and Spectral Analysis_, 2016 (7): 2169-2172; Yun Zhou, Fei Chen, Jianguo Yao, et al.; 3D fluorescent features of the organic matters in standards for drinking water quality. _Chinese Journal of Analysis Laboratory_, 2017(4): 412-414; C. S. M. Figueiró, Oliveira D B D, Russo M R, et al.; and Fish dying water quality monitoring by optical analysis: The potential application of UV-Vis is adsorption and fluorescence spectroscopy, _Aquaculture_, 2018, 490). However, in order to obtain the 3D fluorescence spectrum of the sample, a series of cumbersome procedures such as sample pretreatment, fluorescence spectrophotometer detection, and data processing and mapping. The cumbersome procedures of sample data analysis of conventional fluorescence spectrum lack advantages over the laboratory chemical detection.

The optimization of the cumbersome procedures of sample data analysis is the key for efficiently detecting groundwater using the fluorescence spectrum. Therefore, it is urgent to develop a detection method which can make full use of the advantages of fluorescence spectrum technology in sample detection such as rapid detection, no need of chemical reagents, simple operation and high detection sensitivity.

SUMMARY

The object of the present invention is to provide a rapid detection method for a condition of landfill leachate polluting groundwater, and an application thereof. The rapid detection method provided by the present invention establishes characteristic fluorescence spectrum regions, fluorescence intensities and regular characteristics thereof of organic matters in leachate-polluted groundwater near a landfill in a fluorescence spectrum region, and can achieve the rapid detection of a condition of landfill leachate polluting groundwater by means of a portable fluorescence detector on site. The detection method provided by the present invention is characterized by rapid detection, no need of chemical reagents, simple operation, high detection sensitivity and lower cost.

To achieve the objects, the present invention adopts the technical solutions described below.

In a first aspect, the present invention provides a rapid detection method for a condition of landfill leachate polluting groundwater. The rapid detection method includes: carrying out fluorescence detection on groundwater in a specific region of a landfill, and determining whether the groundwater is polluted according to a ratio of fluorescence intensities at specific excitation/emission (Ex/Em) wavelengths in a specific fluorescence region.

The present invention makes it possible to accurately determine whether the landfill leachate leaked and polluted the groundwater by performing fluorescence detection on groundwater in a landfill within a specific characteristic region and analyzing the magnitudes of ratios of fluorescence intensities.

Compared with unpolluted groundwater, the landfill leachate or leachate-polluted groundwater have characteristic peaks in specific fluorescent regions, which allows to determine whether the groundwater is polluted by comparing intensities of characteristic peaks of water samples collected from different regions of the landfill in the same fluorescent region or by comparing intensities of characteristic peaks of the same water sample collected from the same region of the landfill in different fluorescent regions.

The detection method in the related art takes hours as detection time, in contract, the detection method provided by the present invention can finish the detection within 15 minutes (min). Accordingly, the detection method provided by the present invention has the advantage of rapid detection and therefore may be referred to as the rapid detection method.

The specific excitation/emission wavelengths refer to specific excitation wavelengths and specific emission wavelengths.

In the present invention, in the rapid detection method, water samples from a site background monitoring well, a pollution monitoring well and a pollution diffusion monitoring well near the landfill are detected respectively, and whether the groundwater is polluted is determined according to a ratio of fluorescence intensities at specific excitation/emission wavelengths in a specific fluorescence region among the site background monitoring well, the pollution monitoring well or the pollution diffusion monitoring well, or whether the groundwater is polluted is determined according to a ratio of fluorescence intensities of the water sample of the site background monitoring well, the pollution monitoring well or the pollution diffusion monitoring well in different specific fluorescence regions.

The site background monitoring well near the landfill is usually located 20 meters (m) to 40 m upstream of the landfill, the pollution monitoring well is located 0 m to 20 m downstream of the landfill, and the pollution diffusion monitoring well is located on both sides of the landfill or 30 m to 50 m downstream of the landfill.

In the present invention, the specific fluorescence region includes a region where the Ex/Em is at 240-260 nanometer (nm)/450 nm.

Preferably, if a ratio of a fluorescence intensity $I_{240-260/450}$ of the pollution monitoring well at 240-260 nm/450 nm to a fluorescence intensity $I_{240-260/450}$ of the site background monitoring well at 240-260 nm/450 nm is greater than 6.8, for example, 6.9, 7, 7.1, 7.3, 7.5, 8, 9, etc., the groundwater is considered to be polluted.

Preferably, if the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is less than 4, for example, 3.9, 3.8, 3.5, 2, 1, etc., the groundwater is considered to be not polluted.

Preferably, if the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is 4 to 6.8, for example, 4.2, 4.3, 4.5, 4.8, 5, 5.2, 5.5, 6, 6.2, 6.5, etc., the ratio of fluorescence intensities of the water samples in the site background monitoring well, the pollution monitoring well and the pollution diffusion monitoring well in different specific fluorescence regions is further measured in order to determine whether the groundwater is polluted.

Preferably, the specific fluorescence region further includes a region where the Ex/Em is at 215-225 nm/335-345 nm and 240-260 nm/410 nm.

Preferably, if a ratio $I_a$ of a fluorescence intensity $I_{215-225/335-345}$ at 215-225 nm/335-345 nm to a fluorescence intensity $I_{240-260/410}$ at 240-260 nm/410 nm of the site background monitoring well, a ratio $I_b$ of a fluorescence intensity $I_{215-225/335-345}$ at 215-225 nm/335-345 nm to a fluorescence intensity $I_{240-260/410}$ at 240-260 nm/410 nm of the pollution monitoring well, and a ratio $I_c$ of a fluorescence intensity $I_{215-225/335-345}$ at 215-225 nm/335-345 nm to a fluorescence intensity $I_{240-260/410}$ at 240-260 nm/410 nm of the pollution diffusion monitoring well are all greater than 1 or all less than 1, the groundwater is considered to be not polluted.

Preferably, if the $I_a$, $I_b$ and $I_c$ are not all greater than 1 or not all less than 1, the groundwater is considered to be polluted.

Preferably, if a ratio of a fluorescence intensity $I_{240-260/410}$ of the pollution monitoring well at 240-260 nm/410 nm to a fluorescence intensity $I_{240-260/410}$ of the site background monitoring well at 240-260 nm/410 nm is greater than 6.8, for example, 6.9, 7, 7.1, 7.3, 7.5, 8, 9, etc., the groundwater is considered to be polluted.

Preferably, if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is less than 4, for example, 3.9, 3.8, 3.5, 2, 1, etc., the groundwater is considered to be not polluted.

Preferably, if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is 4 to 6.8, for example, 4.2, 4.3, 4.5, 4.8, 5, 5.2, 5.5, 6, 6.2, 6.5, etc., and the $I_a$, $I_b$ and $I_c$ are all greater than 1 or all less than 1, the groundwater is considered to be not polluted.

Preferably, if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is 4 to 6.8, and the $I_a$, $I_b$ and $I_c$ are not all greater than 1 or not all less than 1, the groundwater is considered to be polluted.

Preferably, in water sample detection of the pollution monitoring well, if $I_{240-260/450}/I_{240-260/410} \leq 1$, for example, 1.5, 2, 3, 4, etc., the groundwater is considered to be polluted.

Preferably, in water sample detection of the pollution diffusion monitoring well, if $I_{240-260/450}/I_{240-260/410} \leq 1$, for example, 1.5, 2, 3, 4, etc., the groundwater is considered to be polluted.

As shown in FIG. 1, the procedure of the rapid detection method is described below.

First, a ratio of a fluorescence intensity $I_{240-260/410}$ of the pollution monitoring well at 240-260 nm/410 nm to a fluorescence intensity $I_{240-260/410}$ of the site background monitoring well at 240-260 nm/410 nm is measured, or a ratio of $I_{240-260/450}$ to $I_{240-260/410}$ in water sample detection of the pollution monitoring well is measured, or a ratio of $I_{240-260/450}$ to $I_{240-260/410}$ in water sample detection of the pollution diffusion monitoring well is measured, and then there are the following situations.

(1) The groundwater has been polluted by the landfill leachate,
    a. if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is greater than 6.8;
    b. if the ratio of $I_{240-260/450}$ to $I_{240-260/410}$ in water sample detection of the pollution monitoring well is greater than or equal to 1; and c. if the ratio of $I_{240-260/450}$ to $I_{240-260/410}$ in water sample detection of the pollution diffusion monitoring well is greater than or equal to 1.

(2) The groundwater is not polluted by the landfill leachate, a. if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is less than 4;

b. if the ratio of $I_{240-260/450}$ to $I_{240-260/410}$ in water sample detection of the pollution monitoring well is less than 1; and c. if the ratio of $I_{240-260/450}$ to $I_{240-260/410}$ in water sample detection of the pollution diffusion monitoring well is less than 1.

(3) When a ratio of a fluorescence intensity $I_{240-260/410}$ of the pollution monitoring well at 240-260 nm/410 nm to a fluorescence intensity $I_{240-260/410}$ of the site background monitoring well at 240-260 nm/410 nm is 4 to 6.8, a ratio $I_a$ of a fluorescence intensity $I_{215-225/335-345}$ at 215-225 nm/335-345 nm to a fluorescence intensity $I_{240-260/410}$ at 240-260 nm/410 nm of the site background monitoring well, a ratio $I_b$ of a fluorescence intensity $I_{215-225/335-345}$ at 215-225 nm/335-345 nm to a fluorescence intensity $I_{240-260/410}$ at 240-260 nm/410 nm of the pollution monitoring well, and a ratio $I_c$ of a fluorescence intensity $I_{215-225/335-345}$ at 215-225 nm/335-345 nm to a fluorescence intensity $I_{240-260/410}$ at 240-260 nm/410 nm of the pollution diffusion monitoring well are further determined, if $I_a$, $I_b$ and $I_c$ are all greater than 1 or all less than 1, the groundwater is considered to be not polluted; and if $I_a$, $I_b$ and $I_c$ are not all greater than 1 or not all less than 1, the groundwater is considered to be polluted.

Of course, $I_a$, $I_b$ and $I_c$ can be directly determined, without determining the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm. In this case, if $I_a$, $I_b$ and $I_c$ are all greater than 1 or all less than 1, the groundwater is considered to be not polluted; if $I_a$, $I_b$ and $I_c$ are not all greater than 1 or not all less than 1, the groundwater is considered to be polluted.

Before the water samples from the site background monitoring well, the pollution monitoring well and the pollution diffusion monitoring well near the landfill are detected, the samples usually need to be simply pretreated. Exemplarily, the samples are filtered using a syringe filtration membrane (0.45 micron (μm)) and a syringe (25 milliliter (mL)).

Preferably, the rapid detection method achieves rapid detection on whether landfill leachate pollutes groundwater by means of a portable fluorescence detector on site.

The rapid detection method provided by the present invention can achieve rapid detection on site (landfill) through the fluorescence detection, preferably by means of a portable fluorescence detector.

In a second aspect, the present invention provides an application of the rapid detection method described in the first aspect in environment monitoring.

Compared with the related art, the present invention has the following beneficial effects.

(1) The rapid detection method provided by the present invention establishes characteristic fluorescence spectrum regions, fluorescence intensities and regular characteristics thereof of organic matters in leachate-polluted groundwater near a landfill in a fluorescence spectrum region, and can achieve the rapid detection of a condition of landfill leachate polluting groundwater by means of a portable fluorescence detector on site.

(2) The detection method provided by the present invention is characterized by rapid detection, no need of chemical reagents, simple operation, high detection sensitivity and lower cost.

DETAILED DESCRIPTION

The technical solutions of the present invention are further described below through specific embodiments. Those skilled in the art should understand that the embodiments are merely used to help understand the present invention and should not be regarded as specific limitations to the present invention.

Embodiment One

A rapid detection method for a condition of landfill leachate polluting groundwater, comprising:

(A) Sample Collection 43 groundwater samples and four landfill leachate samples, 47 samples in total, specifically as follows:

The samples were collected from groundwater in 12 municipal solid waste landfills in 11 counties of China. These landfills were named A, B, C, D, E, F, G, H, I, J, K, and L respectively. Two to five groundwater samples were collected for each landfill from site background monitoring wells (b), pollution monitoring wells (j) and pollution diffusion monitoring wells (k) of the landfills. Thus 43 groundwater samples were collected in total.

Among those, the groundwater of eight landfills, A, B, C, D, E, G, H and I, had not been polluted by the landfill leachate, while the groundwater section of landfills F, J, K and L had been polluted with the leachate. The sample name, for example, A-b, means a water sample from the site background monitoring well of the landfill A, A-j1 means a water sample from the No. 1 pollution monitoring well of the landfill A, A-j2 means a water sample from the No. 2 pollution monitoring well of the landfill A, A-k1 means a water sample from the No. 1 pollution diffusion monitoring well of the landfill A, and A-k2 means a water sample from the No. 2 pollution diffusion monitoring well of the landfill A. The other samples were numbered in the similar way.

Four leachate samples were further collected from four landfills B, J, K and L, which were named BL, JL, KL and LL respectively.

(B) Sample Detection, Comprising Steps of:

(1) The samples were filtered using a syringe filtration membrane (0.45 μm) and a syringe (25 mL); and (2) The Ex/Em wavelengths of the samples were selected within ranges of 215-225 nm/335-345 nm, 240-260 nm/410 nm and 240-260 nm/450 nm, and intensities $I_{220/345}$ at Ex/Em=220 nm/345 nm, $I_{250/410}$ at Ex/Em=250 nm/410 nm, and $I_{250/450}$ at Ex/Em=250 nm/450 nm were measured.

The detection results are shown in FIGS. 2A to 2L, FIG. 3 and Table 1.

Figure 1:
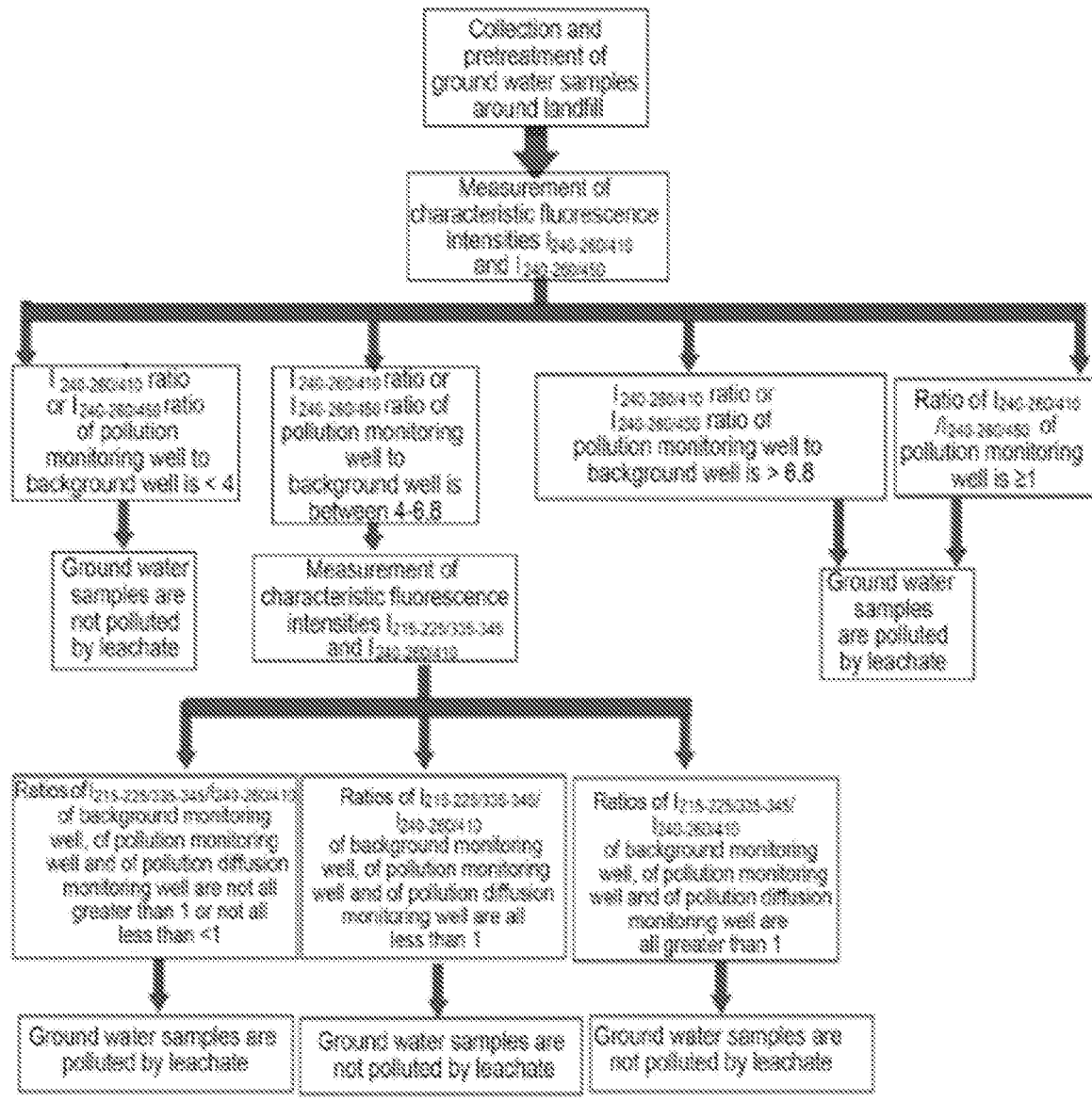
FIG. 1 is a flowchart of a rapid detection method for determining whether groundwater is polluted by landfill leachate according to the present invention.
Figure 2A:
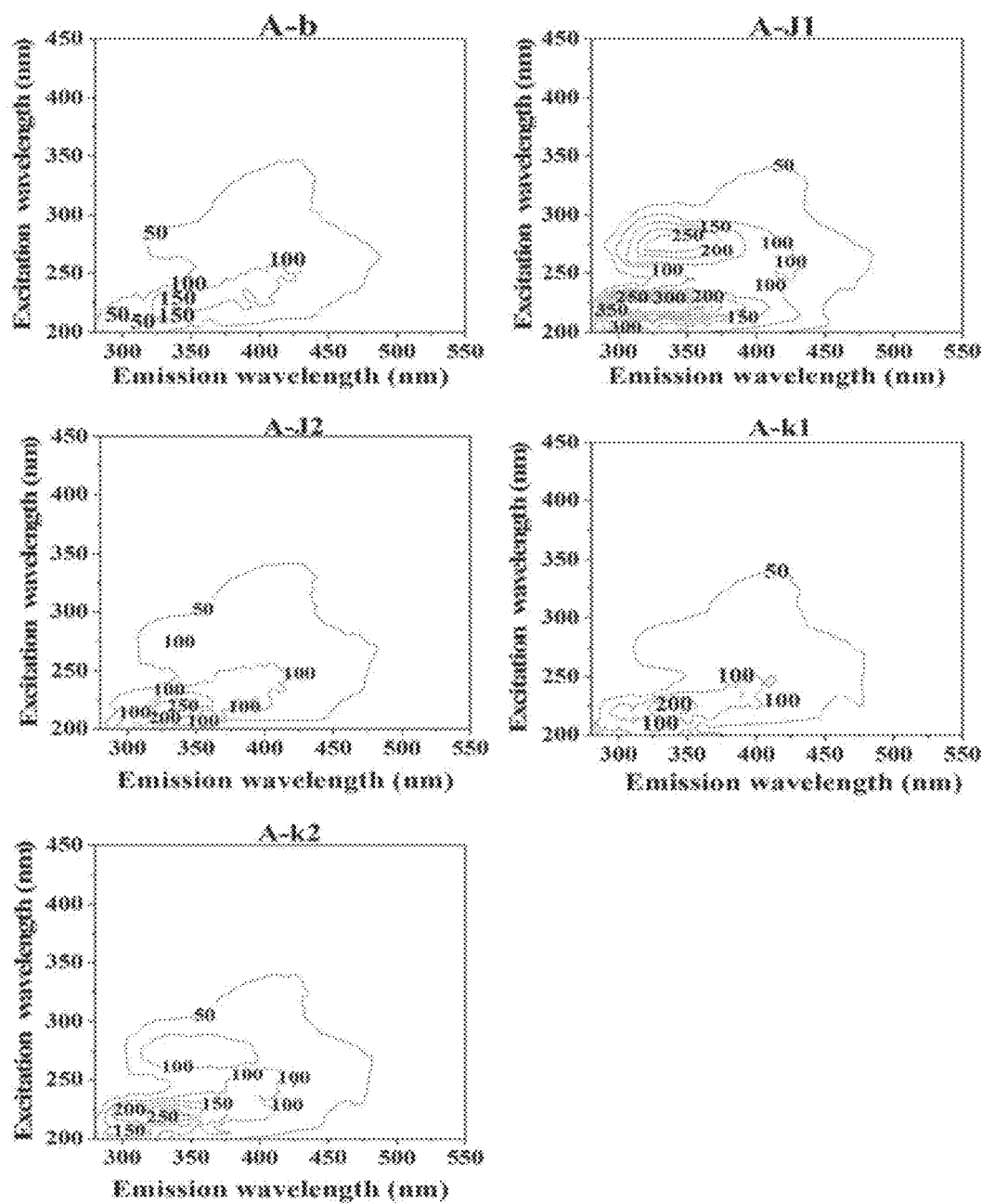
FIG. 2A illustrates three-dimensional fluorescence spectrums of groundwater samples from a landfill A in Embodiment one of the present invention.
Figure 2B:
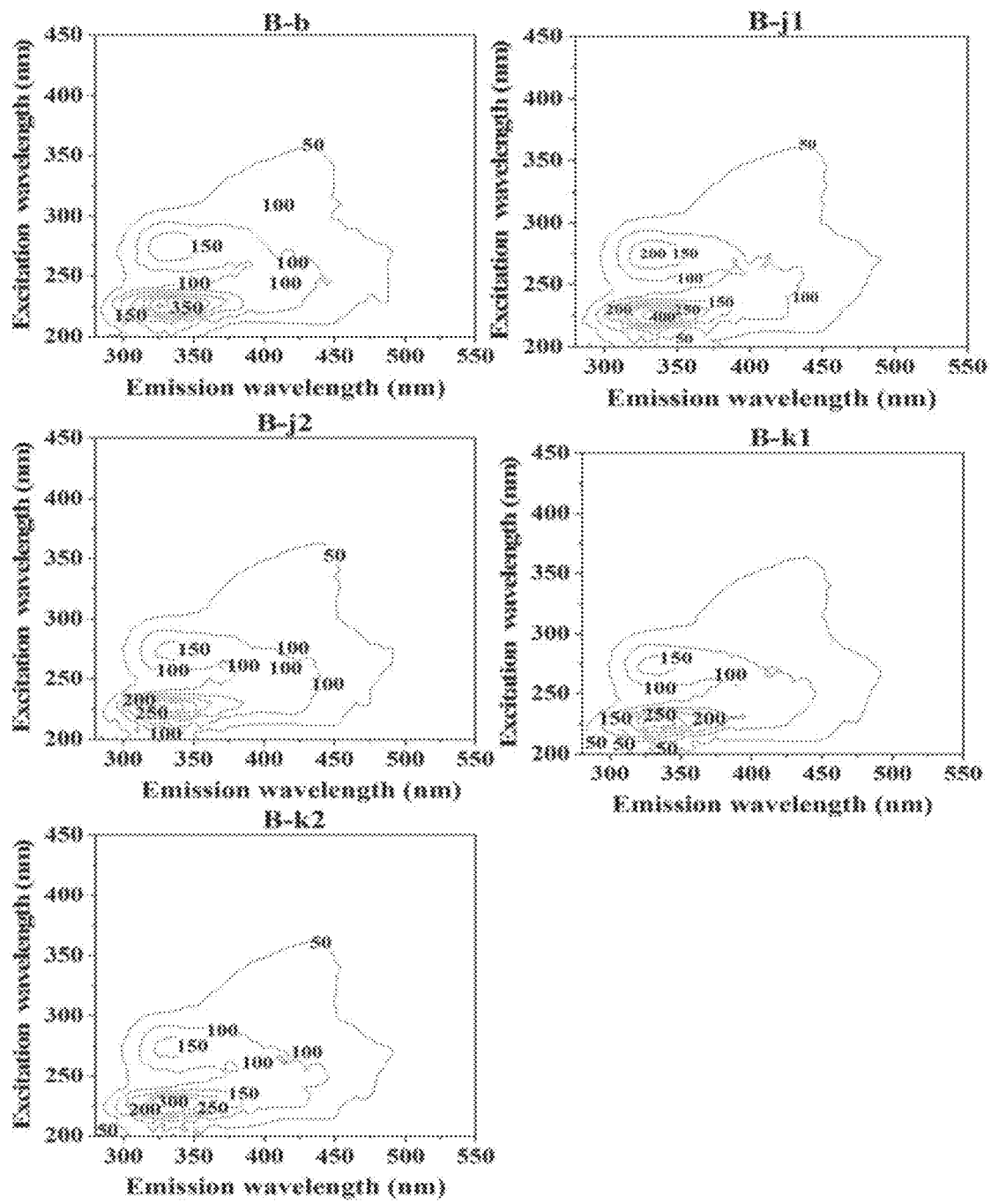
FIG. 2B illustrates three-dimensional fluorescence spectrums of groundwater samples from a landfill B in Embodiment one of the present invention.
Figure 2C:
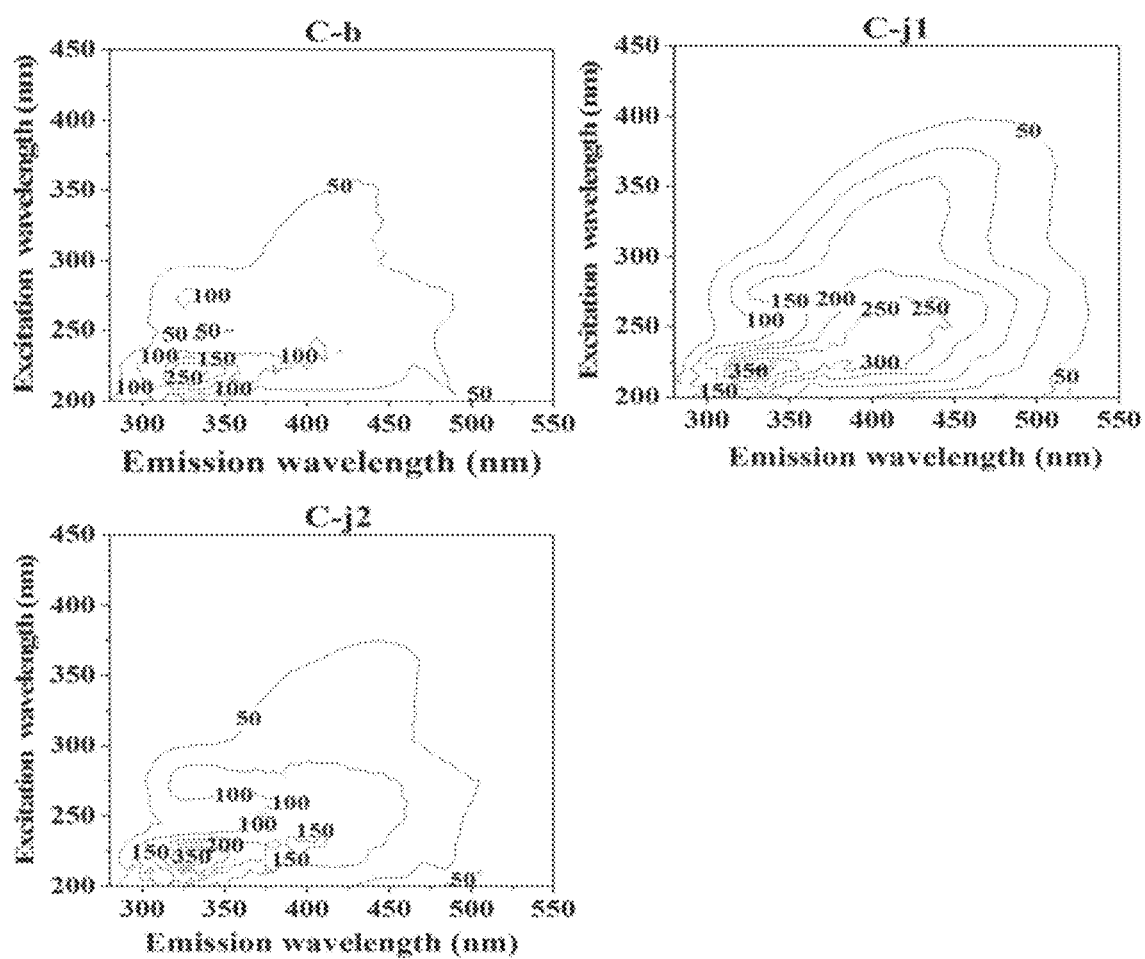
FIG. 2C illustrates three-dimensional fluorescence spectrums of groundwater samples from a landfill C in Embodiment one of the present invention.
Figure 2D:
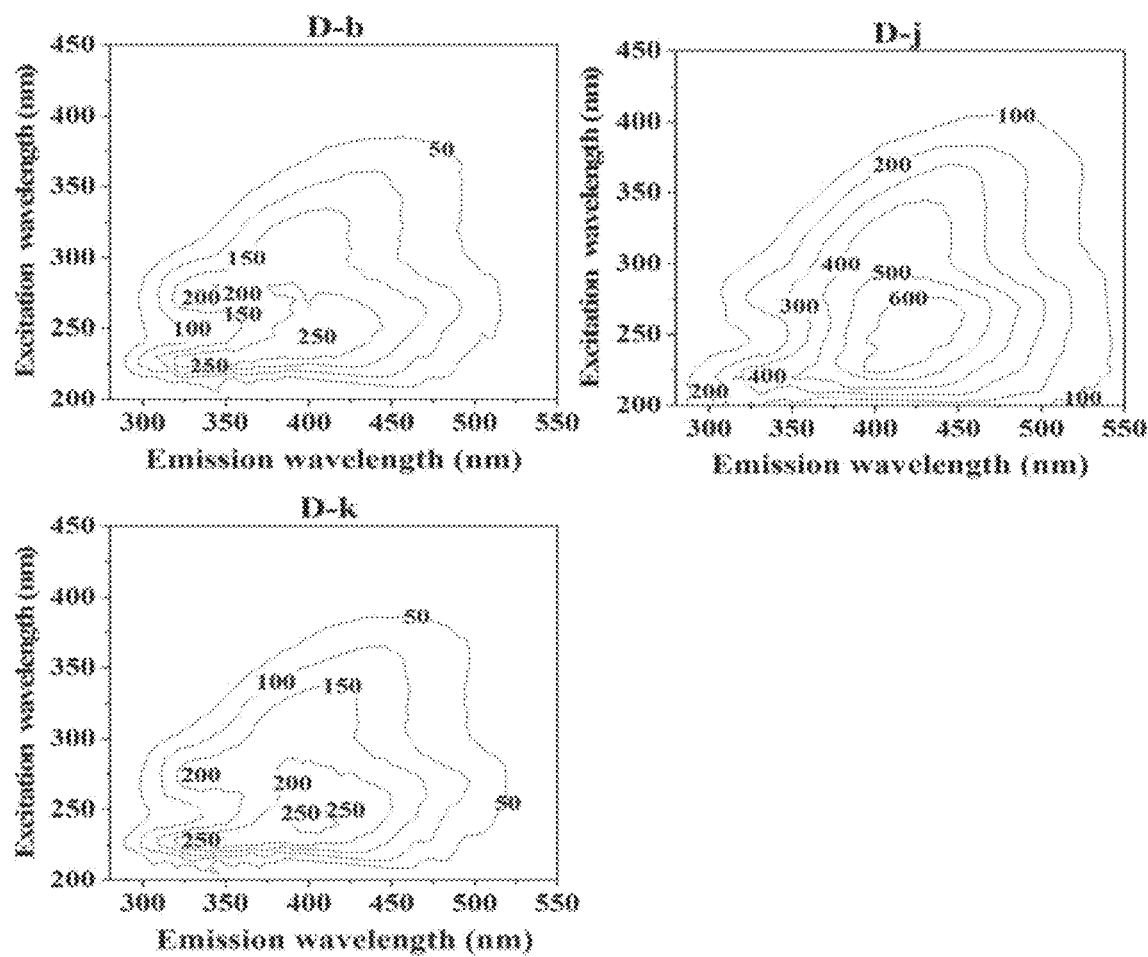
FIG. 2D illustrates three-dimensional fluorescence spectrums of groundwater samples from a landfill D in Embodiment one of the present invention.
Figure 2E:
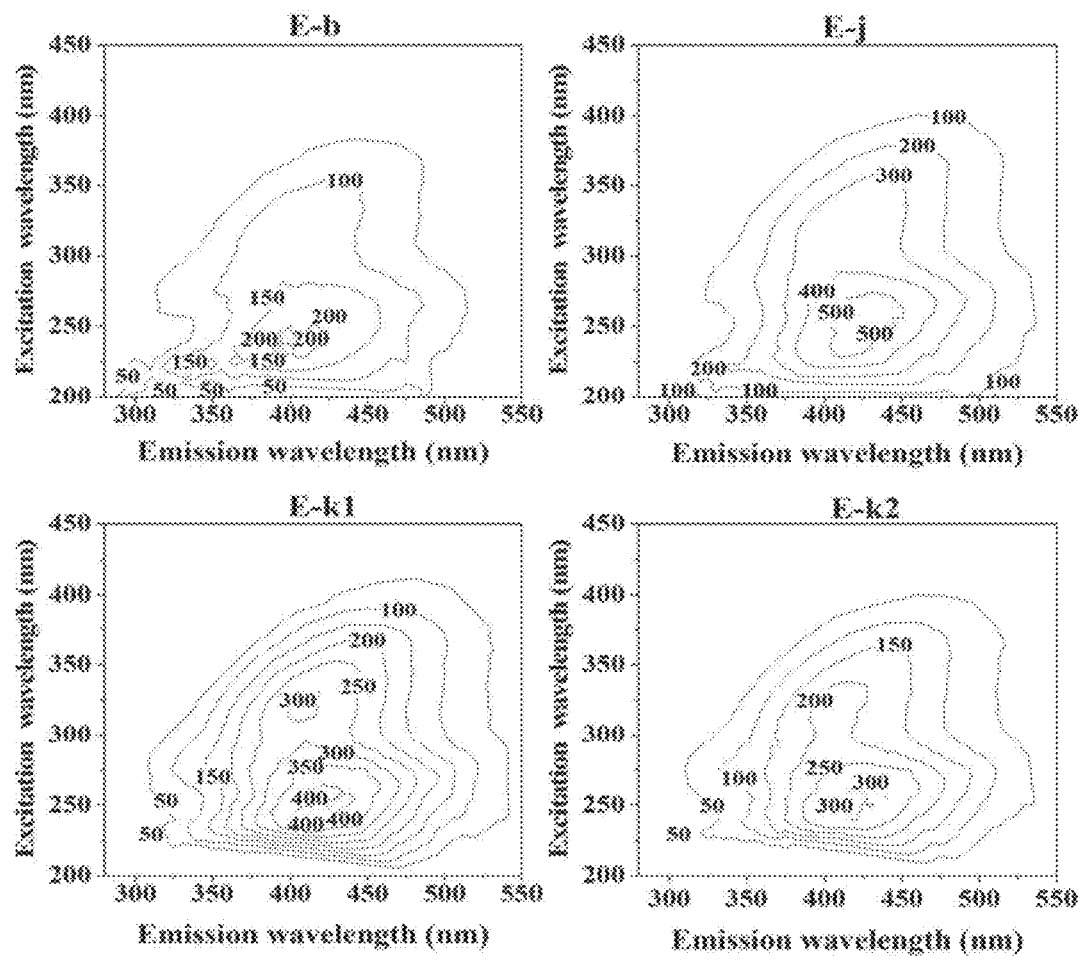
FIG. 2E illustrates three-dimensional fluorescence spectrums of groundwater samples from a landfill E in Embodiment one of the present invention.
Figure 2F:
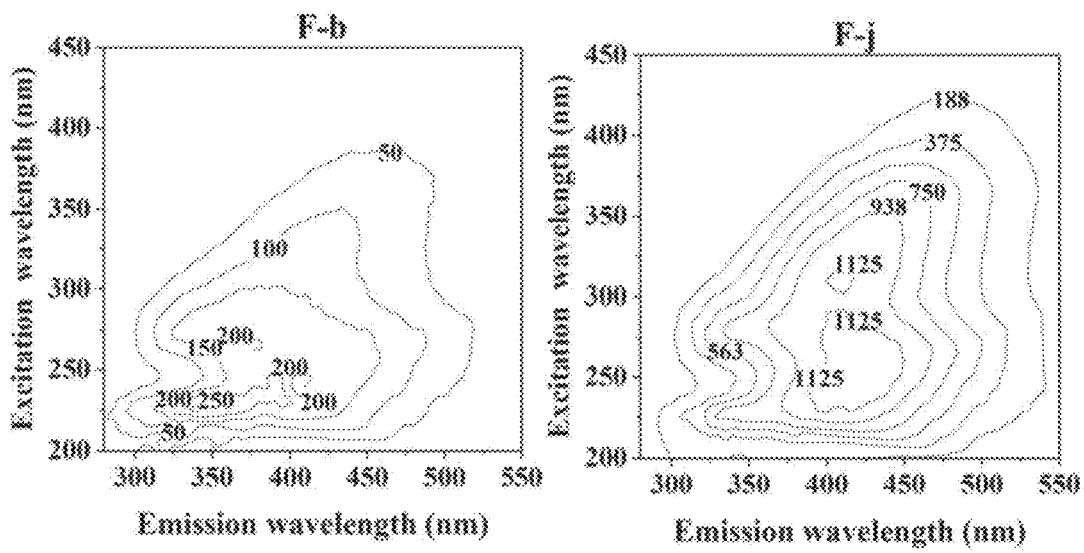
FIG. 2F illustrates three-dimensional fluorescence spectrums of groundwater samples from a landfill F in Embodiment one of the present invention.
Figure 2G:
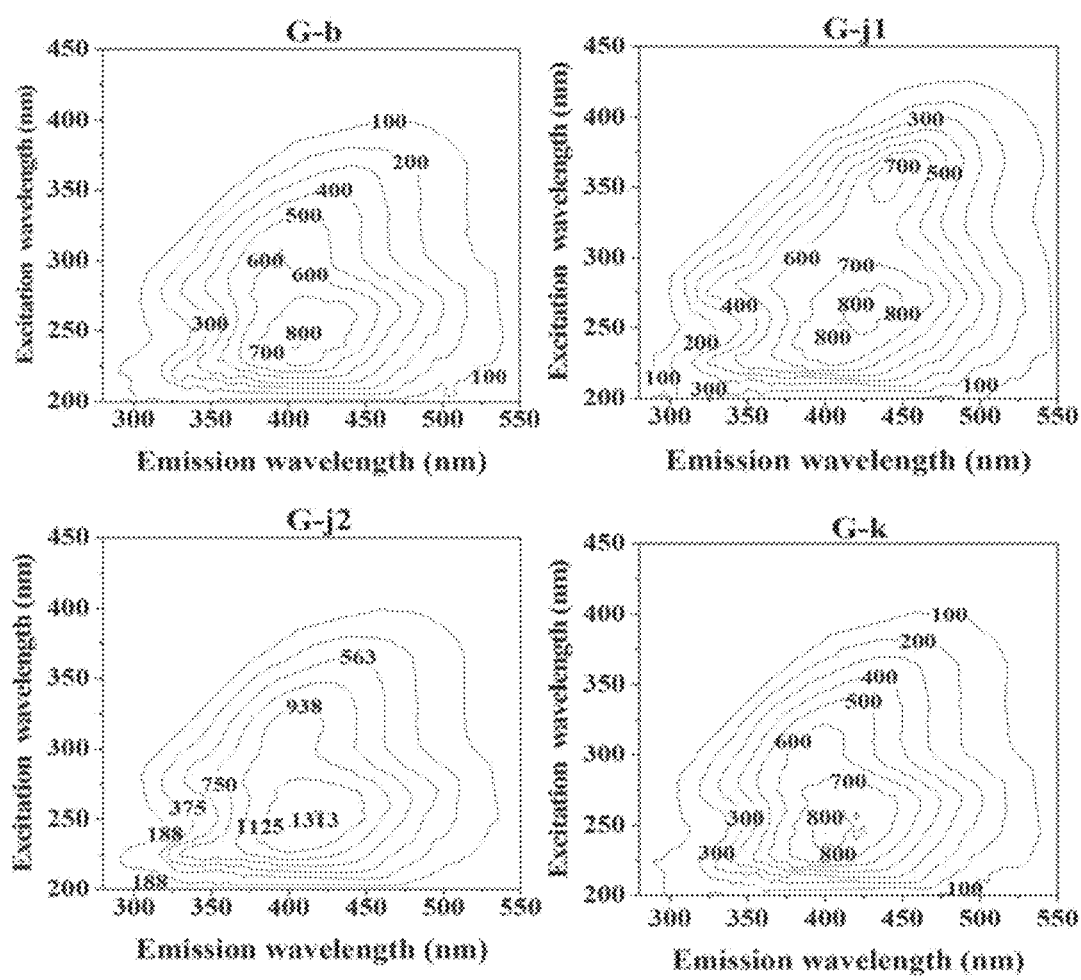
FIG. 2G illustrates three-dimensional fluorescence spectrums of groundwater samples from a landfill G in Embodiment one of the present invention.
Figure 2H:
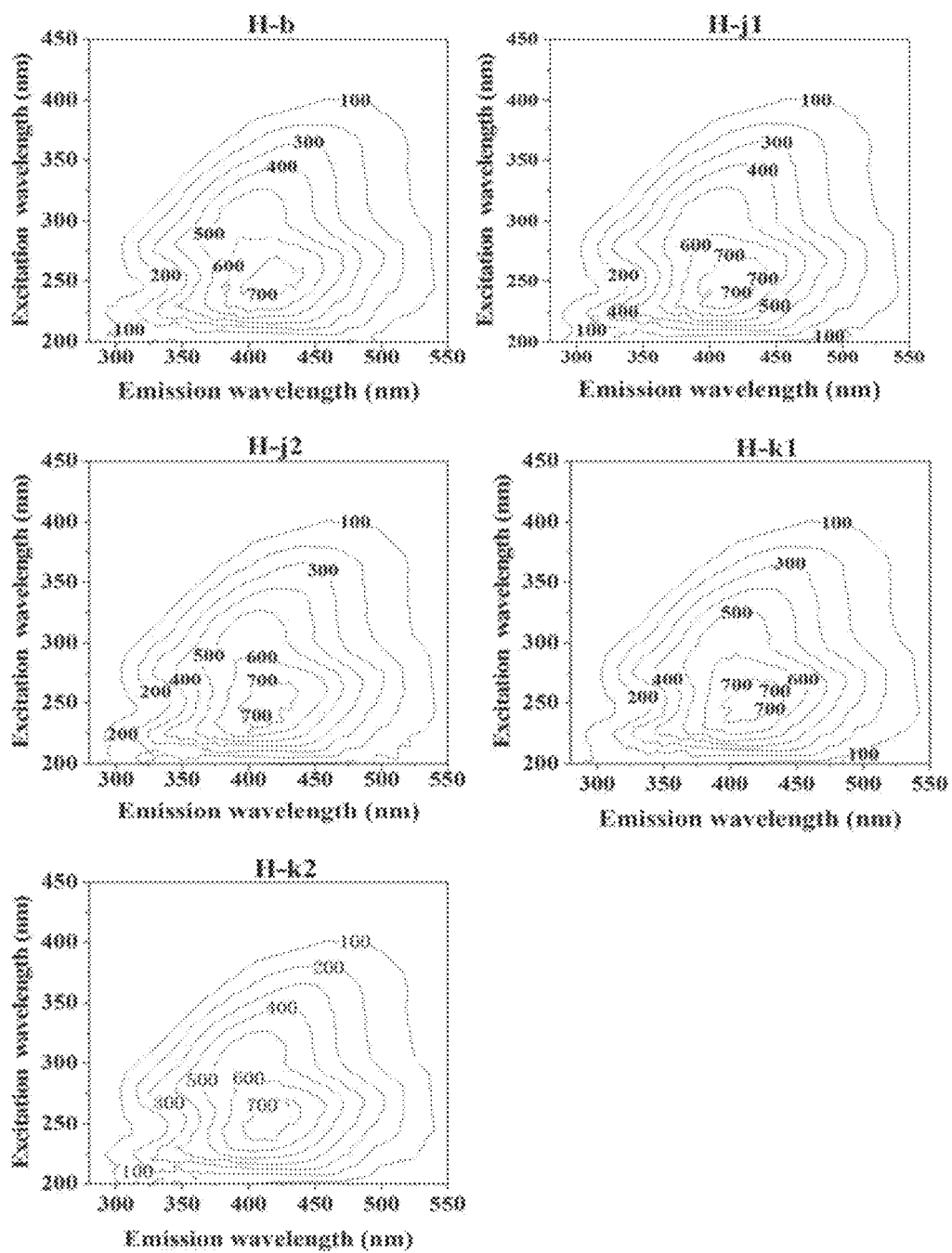
FIG. 2H illustrates three-dimensional fluorescence spectrums of groundwater samples from a landfill H in Embodiment one of the present invention.
Figure 2I:
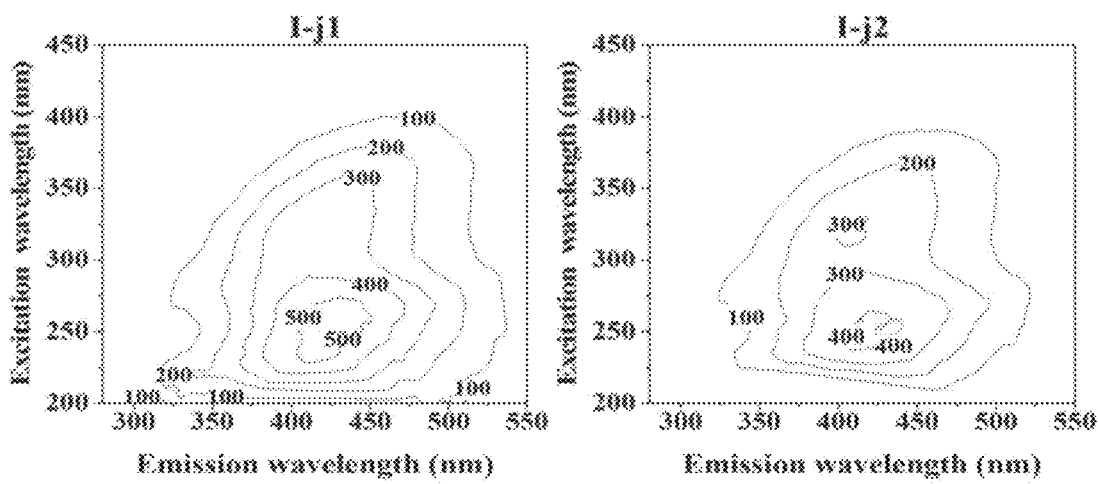
FIG. 2I illustrates three-dimensional fluorescence spectrums of groundwater samples from a landfill I in Embodiment one of the present invention.
Figure 2J:
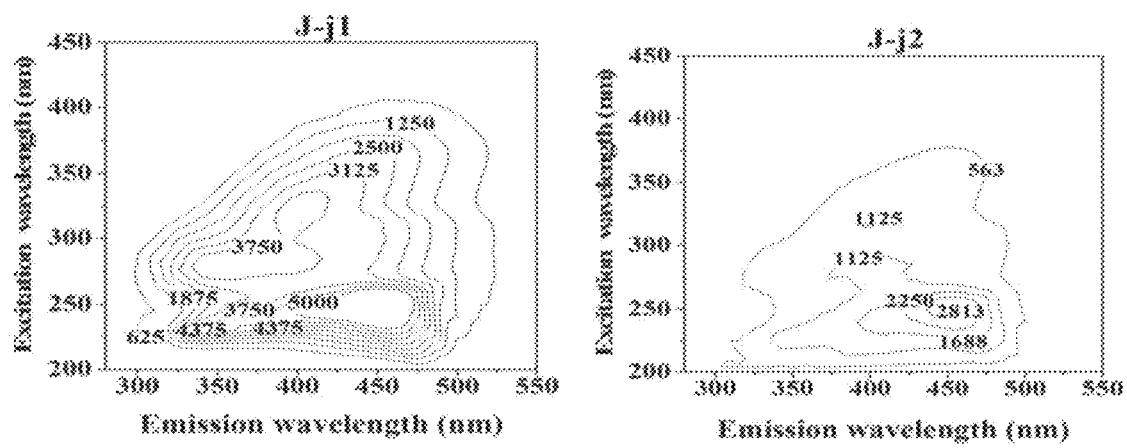
FIG. 2J illustrates three-dimensional fluorescence spectrums of groundwater samples from a landfill J in Embodiment one of the present invention.
Figure 2K:
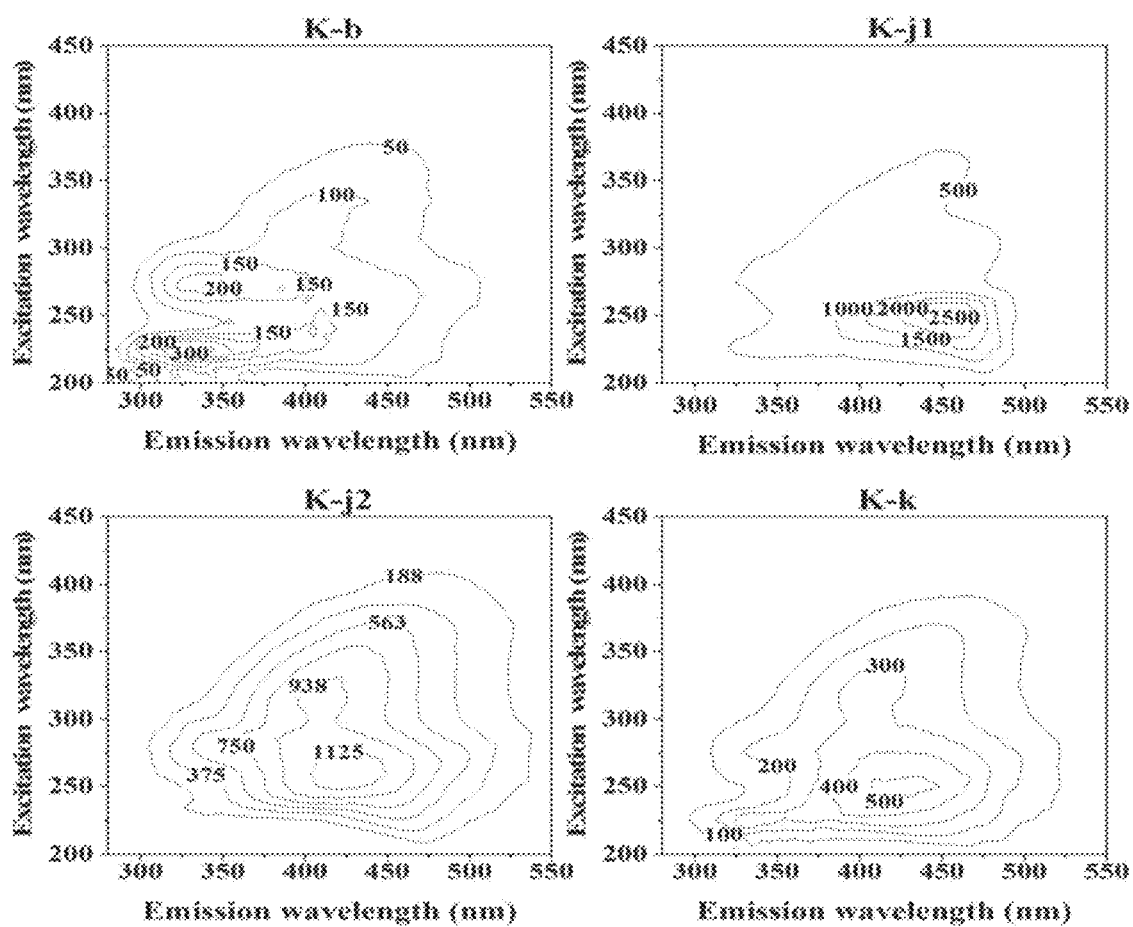
FIG. 2K illustrates three-dimensional fluorescence spectrums of groundwater samples from a landfill K in Embodiment one of the present invention.
Figure 2L:
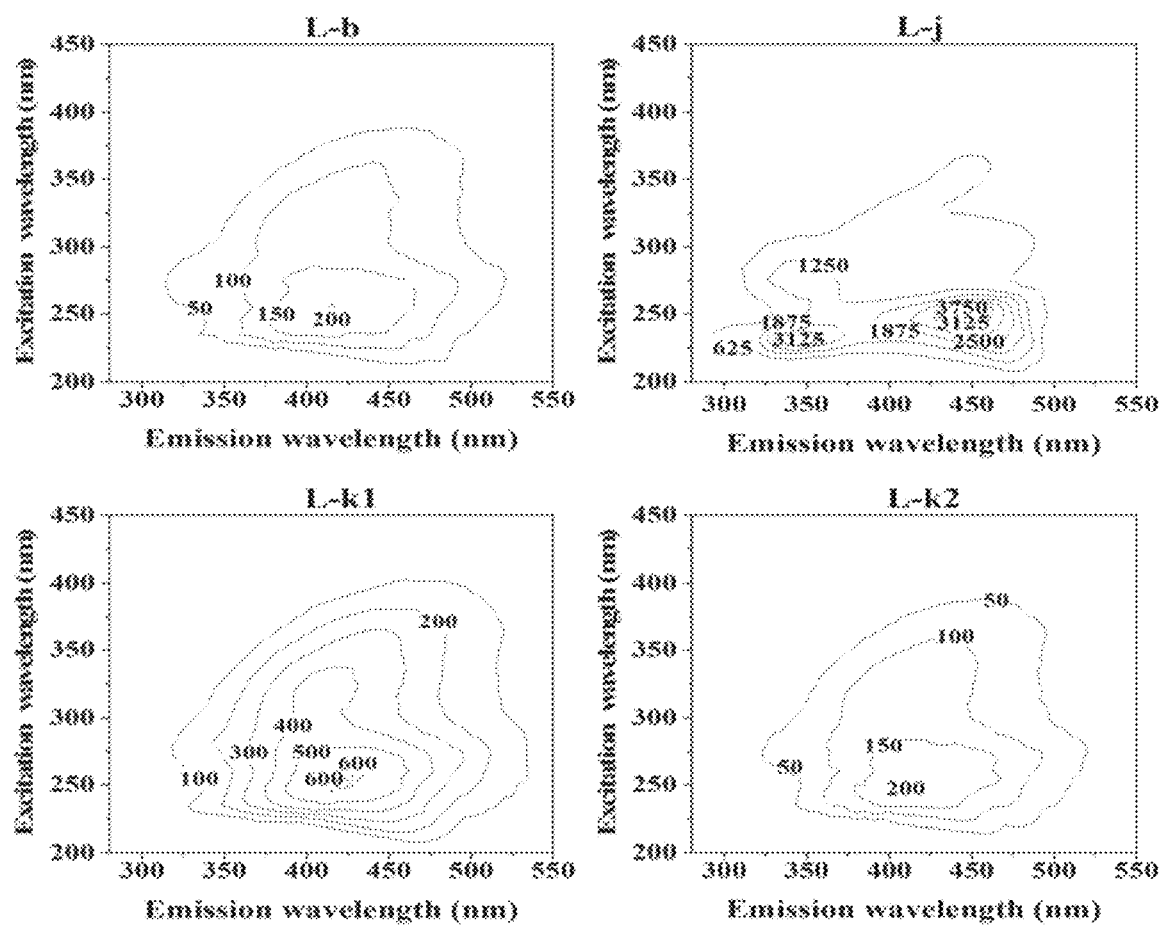
FIG. 2L illustrates three-dimensional fluorescence spectrums of groundwater samples from a landfill L in Embodiment one of the present invention.
Figure 3:
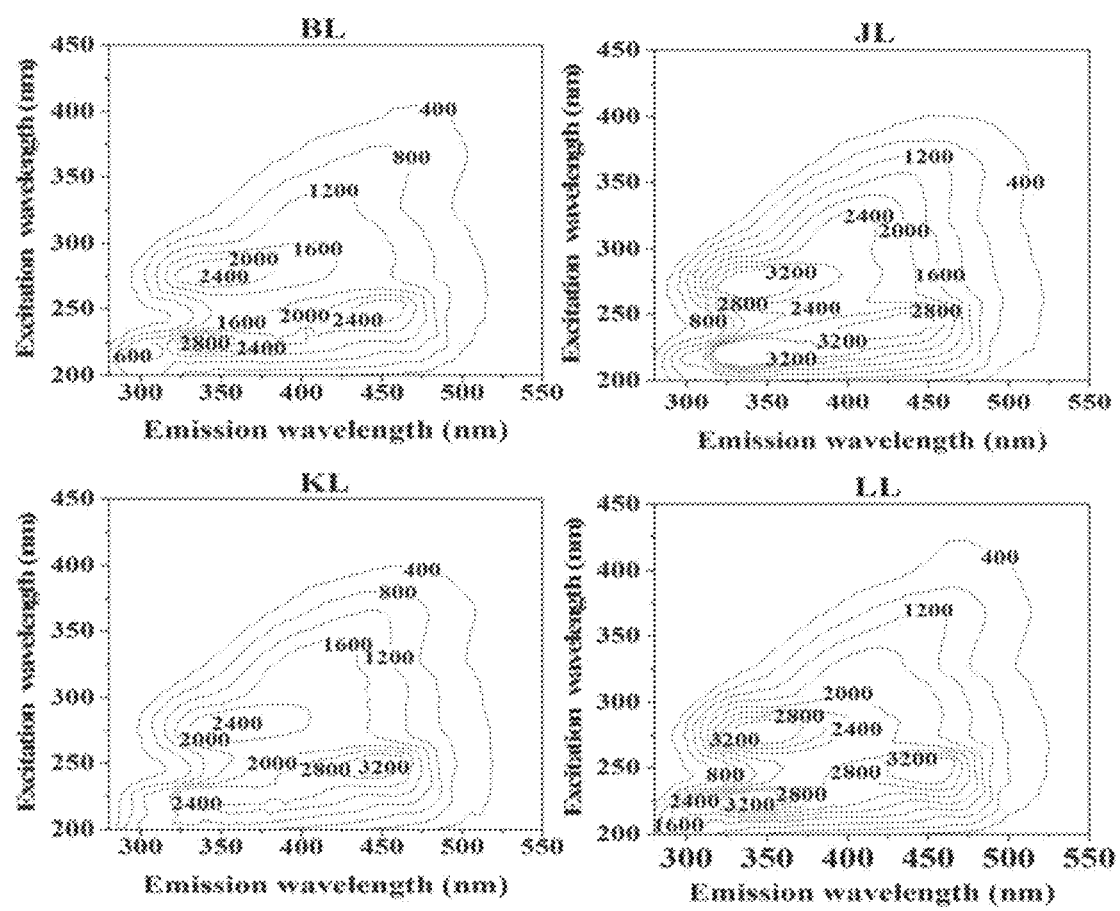
FIG. 3 illustrates three-dimensional fluorescence spectrums of leachate samples from four landfills B, J, K and L in Embodiment one of the present invention.

FIGS. 2A to 2L illustrate three-dimensional fluorescence spectrums of 43 groundwater samples, and FIG. 3 illustrates three-dimensional fluorescence spectrums of four leachate samples. It can be seen from these figures that the regions of the fluorescence peaks in the three-dimensional fluorescence spectrums of the groundwater which has not been polluted by the leachate in the same landfill collected from the site background monitoring well, the pollution monitoring well and the pollution diffusion monitoring well are similar, and the fluorescence intensities are at the same level, which indicates that the composition and the concentration of organic matters are similar. If the groundwater in the same landfill has been polluted by the leachate, regions of the fluorescence peaks in three-dimensional fluorescence spectrums of the groundwater collected from the site background monitoring well, the pollution monitoring well and the pollution diffusion monitoring well have great difference, and the fluorescence intensities are not at the same level, which indicates that the composition and the concentration of organic matters are significantly different.

TABLE 1

| Ex/Em | A-b | A-j1 | A-j2 | A-k1 | A-k2 | B-b | B-j1 | B-j2 |
|---|---|---|---|---|---|---|---|---|
| $I_{220/345}$ | 148.50 | 442.50 | 250.70 | 182.0 | 247.80 | 291.20 | 304.90 | 222.70 |
| $I_{250/410}$ | 103.80 | 108.40 | 104.10 | 102.0 | 107.50 | 107.20 | 113.50 | 121.20 |
| $I_{250/450}$ | 88.11 | 75.13 | 75.70 | 78.42 | 82.08 | 87.390 | 91.84 | 94.47 |
| $I_{220/345}/I_{250/410}$ | 1.43 | 4.08 | 2.41 | 1.78 | 2.31 | 2.720 | 2.69 | 1.84 |
| $I_{250/450}/I_{250/410}$ | 0.85 | 0.69 | 0.73 | 0.77 | 0.76 | 0.82 | 0.81 | 0.78 |

| Ex/Em | B-k1 | B-k2 | C-b | C-j1 | C-j2 | D-b | D-j | D-k |
|---|---|---|---|---|---|---|---|---|
| $I_{220/345}$ | 215.60 | 253.30 | 247.20 | 347.90 | 315.50 | 143.0 | 396.40 | 192.20 |
| $I_{250/410}$ | 113.50 | 114.10 | 93.970 | 281.0 | 133.20 | 247.70 | 665.40 | 247.30 |
| $I_{250/450}$ | 89.2 | 95.47 | 78.66 | 242.40 | 108.80 | 183.70 | 587.20 | 201.00 |
| $I_{220/345}/I_{250/410}$ | 1.90 | 2.22 | 2.63 | 1.24 | 2.37 | 0.58 | 0.60 | 0.78 |
| $I_{250/450}/I_{250/410}$ | 0.79 | 0.84 | 0.84 | 0.86 | 0.82 | 0.74 | 0.89 | 0.88 |

| Ex/Em | E-b | E-j | E-k1 | E-k2 | F-b | F-j | G-b | G-j1 |
|---|---|---|---|---|---|---|---|---|
| $I_{220/345}$ | 150.70 | 229.90 | 2.50 | 27.73 | 185.00 | 613.30 | 335.40 | 413.00 |
| $I_{250/410}$ | 191.10 | 509.60 | 309.00 | 398.40 | 190.50 | 1231.00 | 797.90 | 828.00 |
| $I_{250/450}$ | 160.30 | 455.30 | 261.60 | 361.60 | 163.20 | 1093.00 | 635.60 | 727.80 |
| $I_{220/345}/I_{250/410}$ | 0.79 | 0.45 | 0.01 | 0.07 | 0.97 | 0.50 | 0.42 | 0.50 |
| $I_{250/450}/I_{250/410}$ | 0.84 | 0.89 | 0.85 | 0.91 | 0.86 | 0.89 | 0.85 | 0.82 |

| Ex/Em | G-j2 | G-k | H-b | H-j1 | H-j2 | H-k1 | H-k2 | I-j1 |
|---|---|---|---|---|---|---|---|---|
| $I_{220/345}$ | 679.00 | 353.00 | 310.90 | 330.20 | 377.40 | 383.70 | 336.50 | 229.90 |
| $I_{250/410}$ | 1320.00 | 817.70 | 739.20 | 754.00 | 753.80 | 751.00 | 734.70 | 509.60 |
| $I_{250/450}$ | 1127.00 | 670.70 | 615.80 | 627.70 | 618.90 | 626.60 | 611.00 | 455.30 |
| $I_{220/345}/I_{250/410}$ | 0.51 | 0.43 | 0.42 | 0.44 | 0.50 | 0.51 | 0.46 | 0.45 |
| $I_{250/450}/I_{250/410}$ | 0.85 | 0.82 | 0.83 | 0.83 | 0.82 | 0.83 | 0.83 | 0.89 |

| Ex/Em | I-j2 | J-j1 | J-j2 | K-b | K-j1 | K-j2 | K-k | L-b |
|---|---|---|---|---|---|---|---|---|
| $I_{220/345}$ | 27.73 | 1293.00 | 1113.00 | 261.10 | 556.90 | 41.45 | 269.60 | 26.10 |
| $I_{250/410}$ | 398.40 | 5240.00 | 1848.00 | 153.60 | 1572.00 | 1139.00 | 525.10 | 192.50 |
| $I_{250/450}$ | 361.60 | 7903.00 | 3238.00 | 119.70 | 2883.00 | 1023.00 | 497.20 | 158.30 |
| $I_{220/345}/I_{250/410}$ | 0.07 | 0.25 | 0.60 | 1.70 | 0.35 | 0.04 | 0.51 | 0.14 |
| $I_{250/450}/I_{250/410}$ | 0.91 | 1.51 | 1.75 | 0.78 | 1.83 | 0.90 | 0.95 | 0.82 |

TABLE 1-continued

| Ex/Em | L-j | L-k1 | L-k2 | BL | JL | KL | LL |
|---|---|---|---|---|---|---|---|
| $I_{220/345}$ | 1026.00 | 6.70 | 16.56 | 2061.00 | 4649.00 | 2472.00 | 3914.00 |
| $I_{250/410}$ | 2342.00 | 600.00 | 205.10 | 1951.00 | 3110.00 | 2493.00 | 2580.00 |
| $I_{250/450}$ | 4348.00 | 533.70 | 169.80 | 2764.00 | 3585.00 | 3284.00 | 3660.00 |
| $I_{220/345}/I_{250/410}$ | 0.44 | 0.01 | 0.08 | 1.06 | 1.49 | 0.99 | 1.10 |
| $I_{250/450}/I_{250/410}$ | 1.86 | 0.89 | 0.83 | 1.42 | 1.15 | 1.32 | 1.41 |

Results of $I_{250/410}$ ratio and $I_{250/450}$ ratio of the monitoring well to the background monitoring well for the same landfill are shown in Table 2.

TABLE 2

| Ex/Em | A-j1/A-b | A-j2/A-b | B-j1/B-b | B-j2/B-b | C-j1/C-b |
|---|---|---|---|---|---|
| $I_{250/410}$ | 1.04 | 1.00 | 1.06 | 1.13 | 2.99 |
| $I_{250/450}$ | 0.85 | 0.86 | 1.05 | 1.08 | 3.08 |

| Ex/Em | C-j2/C-b | D-j1/D-b | E-j/E-b | F-j/F-b | G-j1/G-b |
|---|---|---|---|---|---|
| $I_{250/410}$ | 3.36 | 2.69 | 2.67 | 6.46 | 1.04 |
| $I_{250/450}$ | 1.38 | 3.20 | 2.84 | 6.70 | 1.15 |

| Ex/Em | G-j2/G-b | H-j1/H-b | H-j2/H-b | K-j1/K-b | K-j2/K-b |
|---|---|---|---|---|---|
| $I_{250/410}$ | 1.65 | 1.02 | 0.51 | 10.23 | 7.42 |
| $I_{250/450}$ | 1.77 | 1.02 | 1.01 | 24.09 | 8.55 |

| Ex/Em | L-j/L-b |
|---|---|
| $I_{250/410}$ | 12.17 |
| $I_{250/450}$ | 27.47 |

In Table 2, for wells in the landfill F, since the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is between 4 and 6.8, the magnitude of the ratio of the fluorescence intensity $I_{215-225/335}$ at 215-225 nm/335 nm to the fluorescence intensity $I_{240-260/410}$ at 240-260 nm/410 nm of the water sample from the site background monitoring well, the pollution monitoring well or the pollution diffusion monitoring well needs to be determined. Therefore, two more sets of data of the site background monitoring well and the pollution monitoring well were added, as shown in Table 2-2.

TABLE 2-2

| Ex/Em | F-b | | F-j | |
|---|---|---|---|---|
| $I_{225/345}$ | 261.4 | 185.00 | 859.6 | 613.30 |
| $I_{240/410}$ | 195.6 | 190.50 | 1204 | 1231.00 |
| $I_{220/345}/I_{250/410}$ | 1.34 | 0.97 | 0.71 | 0.50 |

As can be seen from tables 1, 2 and 2-2, the detection data analysis for fluorescence of specific wavelengths of groundwater samples from eight landfills without leachate pollution (A, B, C, D, E, G, H, and I), groundwater samples from four landfills with leachate pollution (F, J, K and L) and leachate samples from four landfills indicates that for the groundwater from the landfill without leachate pollution, if the ratio of the intensity $I_{250/410}$ of the pollution monitoring well to the intensity $I_{250/410}$ of the site background monitoring well and the ratio of the intensity $I_{250/450}$ of the pollution monitoring well to the intensity $I_{250/450}$ of the site background monitoring well are both less than 4; for the groundwater from the landfill with leachate pollution, if the ratio of the intensity $I_{250/410}$ of the pollution monitoring well to the intensity $I_{250/410}$ of the site background monitoring well and the ratio of the intensity $I_{250/450}$ of the pollution monitoring well to the intensity $I_{250/450}$ of the site background monitoring well are both greater than 6.8, the groundwater is considered to be polluted; when the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is 4 to 6.8, the magnitude of the ratios of the fluorescence intensity $I_{215-225/335}$ at 215-225 nm/335 nm to the intensity $I_{240-260/410}$ at 240-260 nm/410 nm of the water samples from the site background monitoring well, the pollution monitoring well or the pollution diffusion monitoring well needs to be further determined, and if the ratios are all greater than 1 or all less than 1, it indicates that the groundwater is not polluted, while if the ratios are not all greater than 1 or not all less than 1, it indicates that the groundwater is polluted; if the ratios of $I_{250/450}/I_{250/410}$ of the groundwater from the pollution monitoring well without leachate pollution are all less than 1, and the ratios of $I_{250/450}/I_{250/410}$ of the groundwater samples and the leachate samples from the pollution monitoring well of the landfill with leachate pollution are all greater than 1, it also indicates that the groundwater has been polluted.

Embodiment Two

The same as Embodiment one except for step (2) as follows.

The Ex/Em wavelengths of the samples were selected within ranges of 215-225 nm/335-345 nm, 240-260 nm/410 nm and 240-260 nm/450 nm, and intensities $I_{225/345}$ at Ex/Em=225 nm/345 nm, $I_{245/410}$ at Ex/Em=245 nm/410 nm, and $I_{245/450}$ at Ex/Em=245 nm/450 nm were measured.

The detection results are shown in Table 3.

TABLE 3

| Ex/Em | A-b | A-j1 | A-j2 | A-k1 | A-k2 | B-b | B-j1 | B-j2 |
|---|---|---|---|---|---|---|---|---|
| $I_{225/345}$ | 147.30 | 433.90 | 193.60 | 163.20 | 233.80 | 360.80 | 354.30 | 289.80 |
| $I_{245/410}$ | 104.60 | 112.10 | 109.80 | 104.50 | 107.10 | 121.50 | 123.50 | 128.70 |
| $I_{245/450}$ | 80.64 | 68.25 | 77.11 | 71.43 | 76.13 | 94.75 | 88.15 | 89.83 |
| $I_{225/345}/I_{245/410}$ | 1.41 | 3.87 | 1.76 | 1.56 | 2.18 | 2.97 | 2.87 | 2.25 |
| $I_{245/450}/I_{245/410}$ | 0.77 | 0.61 | 0.70 | 0.68 | 0.71 | 0.78 | 0.71 | 0.70 |

TABLE 3-continued

| Ex/Em | B-k1 | B-k2 | C-b | C-j1 | C-j2 | D-b | D-j | D-k |
|---|---|---|---|---|---|---|---|---|
| $I_{225/345}$ | 306.50 | 295.50 | 215.30 | 328.20 | 292.40 | 228.20 | 375.70 | 238.70 |
| $I_{245/410}$ | 132.60 | 125.20 | 92.75 | 287.90 | 134.10 | 236.90 | 652.90 | 269.20 |
| $I_{245/450}$ | 89.13 | 87.01 | 74.72 | 220.50 | 107.98 | 175.80 | 575.91 | 189.78 |
| $I_{225/345}/I_{245/410}$ | 2.31 | 2.36 | 2.32 | 1.14 | 2.18 | 0.96 | 0.58 | 0.89 |
| $I_{245/450}/I_{245/410}$ | 0.67 | 0.70 | 0.81 | 0.77 | 0.81 | 0.74 | 0.88 | 0.70 |

| Ex/Em | E-b | E-j | E-k1 | E-k2 | F-b | F-j | G-b | G-j1 |
|---|---|---|---|---|---|---|---|---|
| $I_{225/345}$ | 150.30 | 190.40 | 100.10 | 47.78 | 264.10 | 859.60 | 430.40 | 505.10 |
| $I_{245/410}$ | 200.50 | 514.50 | 415.10 | 319.30 | 210.40 | 1248.00 | 804.10 | 804.70 |
| $I_{245/450}$ | 161.71 | 452.41 | 346.74 | 249.16 | 152.90 | 1034.00 | 616.51 | 685.90 |
| $I_{225/345}/I_{245/410}$ | 0.75 | 0.37 | 0.24 | 0.15 | 1.26 | 0.69 | 0.54 | 0.63 |
| $I_{245/450}/I_{245/410}$ | 0.81 | 0.88 | 0.84 | 0.78 | 0.73 | 0.83 | 0.77 | 0.85 |

| Ex/Em | G-j2 | G-k | H-b | H-j1 | H-j2 | H-k1 | H-k2 | I-j1 |
|---|---|---|---|---|---|---|---|---|
| $I_{225/345}$ | 850.10 | 472.60 | 384.40 | 410.60 | 442.40 | 407.20 | 369.10 | 190.40 |
| $I_{245/410}$ | 1322.00 | 811.00 | 757.60 | 740.00 | 770.80 | 733.30 | 743.10 | 514.50 |
| $I_{245/450}$ | 1025.20 | 635.02 | 595.88 | 602.07 | 592.81 | 599.09 | 590.67 | 452.41 |
| $I_{225/345}/I_{245/410}$ | 0.64 | 0.58 | 0.51 | 0.55 | 0.57 | 0.56 | 0.50 | 0.37 |
| $I_{245/450}/I_{245/410}$ | 0.78 | 0.78 | 0.79 | 0.81 | 0.77 | 0.82 | 0.79 | 0.88 |

| Ex/Em | I-j2 | J-j1 | J-j2 | K-b | K-j1 | K-j2 | K-k | L-b |
|---|---|---|---|---|---|---|---|---|
| $I_{225/345}$ | 100.10 | 2775.00 | 1290.00 | 307.40 | 814.40 | 96.90 | 356.70 | 20.44 |
| $I_{245/410}$ | 415.10 | 5518.00 | 1993.00 | 152.00 | 1629.00 | 1054.00 | 504.80 | 196.50 |
| $I_{245/450}$ | 346.74 | 7129.30 | 2907.70 | 117.68 | 2595.60 | 939.70 | 449.72 | 167.51 |
| $I_{225/345}/I_{245/410}$ | 0.24 | 0.50 | 0.65 | 2.02 | 0.50 | 0.09 | 0.71 | 0.10 |
| $I_{245/450}/I_{245/410}$ | 0.84 | 1.29 | 1.46 | 0.77 | 1.59 | 0.89 | 0.89 | 0.85 |

| Ex/Em | L-j | L-k1 | L-k2 | BL | JL | KL | LL |
|---|---|---|---|---|---|---|---|
| $I_{225/345}$ | 2189.00 | 68.82 | 18.44 | 2750.00 | 5716.00 | 2711.00 | 3914.00 |
| $I_{245/410}$ | 2457.00 | 590.00 | 194.50 | 2105.00 | 3318.00 | 2708.00 | 2901.00 |
| $I_{245/450}$ | 3909.60 | 516.69 | 154.58 | 2630.50 | 3420.40 | 3090.50 | 3733.20 |
| $I_{225/345}/I_{245/410}$ | 0.89 | 0.12 | 0.09 | 1.31 | 1.72 | 1.00 | 1.35 |
| $I_{245/450}/I_{245/410}$ | 1.59 | 0.88 | 0.79 | 1.25 | 1.03 | 1.14 | 1.29 |

Results of $I_{245/410}$ ratio and $I_{245/450}$ ratio of the monitoring well to the background monitoring well for the same landfill are shown in Table 4.

TABLE 4

| Ex/Em | A-j1/A-b | A-j2/A-b | B-j1/B-b | B-j2/B-b | C-j1/C-b |
|---|---|---|---|---|---|
| $I_{245/410}$ | 1.07 | 1.05 | 1.02 | 1.06 | 3.10 |
| $I_{245/450}$ | 0.85 | 0.96 | 0.93 | 0.95 | 2.95 |

| Ex/Em | C-j2/C-b | D-j1/D-b | E-j/E-b | F-j/F-b | G-j1/G-b |
|---|---|---|---|---|---|
| $I_{245/410}$ | 1.45 | 2.76 | 2.57 | 5.93 | 1.00 |
| $I_{245/450}$ | 1.45 | 3.28 | 2.80 | 6.72 | 1.11 |

| Ex/Em | G-j2/G-b | H-j1/H-b | H-j2/H-b | K-j1/K-b | K-j2/K-b |
|---|---|---|---|---|---|
| $I_{245/410}$ | 1.64 | 0.98 | 1.02 | 10.72 | 6.93 |
| $I_{245/450}$ | 1.66 | 1.01 | 0.99 | 22.06 | 7.99 |

| Ex/Em | L-j/L-b |
|---|---|
| $I_{245/410}$ | 12.50 |
| $I_{245/450}$ | 23.34 |

As can be seen from tables 3 and 4, the detection data analysis for fluorescence at specific wavelengths of groundwater samples from eight landfills without leachate pollution (A, B, C, D, E, G, H, and I), groundwater samples from four landfills with leachate pollution (F, J, K and L) and leachate samples from four landfills indicates that for the groundwater from the landfill without leachate pollution, if the ratio of the intensity $I_{250/410}$ of the pollution monitoring well to the intensity $I_{250/410}$ of the site background monitoring well and the ratio of the intensity $I_{245/450}$ of the pollution monitoring well to the intensity $I_{245/450}$ of the site background monitoring well are both less than 4; for the groundwater from the landfill with leachate pollution, if the ratio of the intensity $I_{245/410}$ of the pollution monitoring well to the intensity $I_{245/410}$ of the site background monitoring well and the ratio of the intensity $I_{245/450}$ of the pollution monitoring well to the intensity $I_{245/450}$ of the site background monitoring well are both greater than 6.8, the groundwater is considered to be polluted; when the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is between 4 and 6.8, the magnitude of the ratios of the fluorescence intensity $I_{215-225/335}$ at 215-225 nm/335 nm to the intensity $I_{240-260/410}$ at 240-260 nm/410 nm of the water samples from the site background monitoring well, the pollution monitoring well or the pollution diffusion monitoring well needs to be further determined, and if the ratios are all greater than 1 or all less than 1, it indicates that the groundwater is not polluted, while if the ratios are not all greater than 1 or not all less than 1, it indicates that the groundwater is polluted; if the ratios of $I_{245/450}/I_{245/410}$ of the groundwater from the pollution monitoring well without leachate pollution are all less than 1, and the ratios of $I_{245/450}/I_{245/410}$ of the groundwater samples and the leachate samples from the pollution monitoring well of the landfill with leachate pollution are all greater than 1, it also indicates that the groundwater has been polluted.

Embodiment Three

The same as Embodiment one except for step (2) as follows.

The Ex/Em wavelengths of the samples were selected within ranges of 215-225 nm/335-345 nm, 240-260 nm/410 nm and 240-260 nm/450 nm, and intensities $I_{225/335}$ at Ex/Em=225 nm/335 nm, $I_{255/410}$ at Ex/Em=255 nm/410 nm, and $I_{255/450}$ at Ex/Em=255 nm/450 nm were measured.

The detection results are shown in Table 5.

Results of $I_{255/410}$ ratio or $I_{255/450}$ ratio of the monitoring well to the background monitoring well for the same landfill are shown in Table 6.

TABLE 6

| Ex/Em | A-j1/A-b | A-j2/A-b | B-j1/B-b | B-j2/B-b | C-j1/C-b |
|---|---|---|---|---|---|
| $I_{255/410}$ | 1.06 | 0.90 | 1.00 | 1.01 | 3.15 |
| $I_{255/450}$ | 0.98 | 0.97 | 0.98 | 1.03 | 2.83 |

| Ex/Em | C-j2/C-b | D-j1/D-b | E-j/E-b | F-j/F-b | G-j1/G-b |
|---|---|---|---|---|---|
| $I_{255/410}$ | 1.55 | 2.77 | 2.71 | 6.40 | 1.02 |
| $I_{255/450}$ | 1.30 | 3.31 | 3.10 | 6.72 | 1.15 |

TABLE 5

| Ex/Em | A-b | A-j1 | A-j2 | A-k1 | A-k2 | B-b | B-j1 | B-j2 |
|---|---|---|---|---|---|---|---|---|
| $I_{225/335}$ | 142.70 | 409.00 | 204.00 | 208.10 | 258.90 | 355.20 | 380.60 | 338.50 |
| $I_{255/410}$ | 107.90 | 113.90 | 97.46 | 92.68 | 110.50 | 107.30 | 106.90 | 108.70 |
| $I_{255/450}$ | 83.85 | 82.45 | 81.26 | 81.43 | 79.57 | 88.23 | 86.34 | 90.71 |
| $I_{225/335}/I_{255/410}$ | 1.32 | 3.59 | 2.09 | 2.25 | 2.34 | 3.31 | 3.56 | 3.11 |
| $I_{255/450}/I_{255/410}$ | 0.78 | 0.72 | 0.83 | 0.88 | 0.72 | 0.82 | 0.81 | 0.83 |

| Ex/Em | B-k1 | B-k2 | C-b | C-j1 | C-j2 | D-b | D-j | D-k |
|---|---|---|---|---|---|---|---|---|
| $I_{225/335}$ | 314.80 | 329.50 | 237.30 | 330.40 | 325.10 | 228.10 | 376.80 | 231.10 |
| $I_{255/410}$ | 117.60 | 103.30 | 90.45 | 285.20 | 140.30 | 231.80 | 642.10 | 237.20 |
| $I_{255/450}$ | 93.82 | 90.91 | 83.93 | 237.20 | 109.00 | 182.60 | 604.60 | 197.80 |
| $I_{225/335}/I_{255/410}$ | 2.68 | 3.19 | 2.62 | 1.16 | 2.32 | 0.98 | 0.59 | 0.97 |
| $I_{255/450}/I_{255/410}$ | 0.80 | 0.88 | 0.93 | 0.83 | 0.78 | 0.79 | 0.94 | 0.83 |

| Ex/Em | E-b | E-j | E-k1 | E-k2 | F-b | F-j | G-b | G-j1 |
|---|---|---|---|---|---|---|---|---|
| $I_{225/335}$ | 152.80 | 173.40 | 94.65 | 47.24 | 249.1 | 762.5 | 359.30 | 473.90 |
| $I_{255/410}$ | 194.20 | 526.30 | 400.70 | 291.50 | 188.7 | 1207 | 779.20 | 795.60 |
| $I_{255/450}$ | 160.70 | 498.60 | 367.20 | 268.30 | 164.5 | 1106 | 654.30 | 753.80 |
| $I_{225/335}/I_{255/410}$ | 0.79 | 0.33 | 0.24 | 0.16 | 1.32 | 0.63 | 0.46 | 0.60 |
| $I_{255/450}/I_{255/410}$ | 0.83 | 0.95 | 0.92 | 0.92 | 0.87 | 0.92 | 0.84 | 0.95 |

| Ex/Em | G-j2 | G-k | H-b | H-j1 | H-j2 | H-k1 | H-k2 | I-j1 |
|---|---|---|---|---|---|---|---|---|
| $I_{225/335}$ | 801.90 | 366.40 | 344.30 | 408.10 | 388.30 | 360.90 | 355.60 | 173.40 |
| $I_{255/410}$ | 1308.00 | 815.40 | 709.40 | 747.00 | 722.90 | 738.60 | 729.30 | 526.30 |
| $I_{255/450}$ | 1088.00 | 672.70 | 633.40 | 650.10 | 623.50 | 652.60 | 624.10 | 498.60 |
| $I_{225/335}/I_{255/410}$ | 0.61 | 0.45 | 0.49 | 0.55 | 0.54 | 0.49 | 0.49 | 0.33 |
| $I_{255/450}/I_{255/410}$ | 0.83 | 0.82 | 0.89 | 0.87 | 0.86 | 0.88 | 0.86 | 0.95 |

| Ex/Em | I-j2 | J-j1 | J-j2 | K-b | K-j1 | K-j2 | K-k | L-b |
|---|---|---|---|---|---|---|---|---|
| $I_{225/335}$ | 94.65 | 2470.00 | 1084.00 | 338.70 | 758.90 | 92.38 | 344.80 | 24.71 |
| $I_{255/410}$ | 400.70 | 4559.00 | 1593.00 | 150.00 | 1309.00 | 1190.00 | 505.50 | 192.70 |
| $I_{255/450}$ | 367.20 | 7161.00 | 2921.00 | 122.20 | 2661.00 | 1073.00 | 492.90 | 174.70 |
| $I_{225/335}/I_{255/410}$ | 0.24 | 0.54 | 0.68 | 2.26 | 0.58 | 0.08 | 0.68 | 0.13 |
| $I_{255/450}/I_{255/410}$ | 0.92 | 1.57 | 1.83 | 0.81 | 2.03 | 0.90 | 0.98 | 0.91 |

| Ex/Em | L-j | L-k1 | L-k2 | BL | JL | KL | LL |
|---|---|---|---|---|---|---|---|
| $I_{225/335}$ | 1974.00 | 53.80 | 7.60 | 2655.00 | 5577.00 | 2612.00 | 3674.00 |
| $I_{255/410}$ | 1923.00 | 601.20 | 194.90 | 1730.00 | 2788.00 | 2250.00 | 2507.00 |
| $I_{255/450}$ | 3954.00 | 533.80 | 181.70 | 2609.00 | 3313.00 | 3022.00 | 3655.00 |
| $I_{225/335}/I_{255/410}$ | 1.03 | 0.09 | 0.04 | 1.53 | 2.00 | 1.16 | 1.47 |
| $I_{255/450}/I_{255/410}$ | 2.06 | 0.89 | 0.93 | 1.51 | 1.19 | 1.34 | 1.46 |

TABLE 6-continued

| Ex/Em | G-j2/G-b | H-j1/H-b | H-j2/H-b | K-j1/K-b | K-j2/K-b |
|---|---|---|---|---|---|
| $I_{255/410}$ | 1.68 | 0.98 | 1.02 | 8.73 | 7.93 |
| $I_{255/450}$ | 1.66 | 1.01 | 0.99 | 21.78 | 8.78 |

| Ex/Em | L-j/L-b |
|---|---|
| $I_{255/410}$ | 9.98 |
| $I_{255/450}$ | 22.63 |

As can be seen from tables 5 and 6, the detection data analysis for fluorescence of specific wavelengths of groundwater samples from nine landfills without leachate pollution (A to I), groundwater samples from three landfills with leachate pollution (J to L) and leachate samples from four landfills indicates that for the groundwater from the landfill without leachate pollution, if the ratio of the intensity $I_{255/410}$ of the pollution monitoring well to the intensity $I_{225/410}$ of the site background monitoring well and the ratio of the intensity $I_{255/450}$ of the pollution monitoring well to the intensity $I_{255/450}$ of the site background monitoring well are both less than 4; for the groundwater from the landfill with leachate pollution, if the ratio of the intensity $I_{225/410}$ of the pollution monitoring well to the intensity $I_{225/410}$ of the site background monitoring well and the ratio of the intensity $I_{255/450}$ of the pollution monitoring well to the intensity $I_{255/450}$ of the site background monitoring well are both greater than 6.8, the groundwater is considered to be polluted; when the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is between 4 and 6.8, the magnitude of the ratios of the fluorescence intensity $I_{215-225/335}$ at 215-225 nm/335 nm to the intensity $I_{240-260/410}$ at 240-260 nm/410 nm of the water samples from the site background monitoring well, the pollution monitoring well or the pollution diffusion monitoring well needs to be further determined, and if the ratios are all greater than 1 or all less than 1, it indicates that the groundwater is not polluted, while if the ratios are not all greater than 1 or not all less than 1, it indicates that the groundwater is polluted; if the ratios of $I_{255/450/1255/410}$ of the groundwater from the pollution monitoring well without leachate pollution are all less than 1, and the ratios of $I_{255/450/1255/410}$ of the groundwater samples and the leachate samples from the pollution monitoring well of the landfill with leachate pollution are all greater than 1, it also indicates that the groundwater has been polluted.

As can be seen from tables 1 to 6, in the rapid detection method provided by the present invention, the fluorescence within the range of 240-260 nm/450 nm, 215-225 nm/335-345 nm and 240-260 nm/410 nm is detected, and whether the groundwater is polluted by the landfill leachate according to the ratio of fluorescence intensities.

Comparative Example One

The same as Embodiment one except that this comparative example determined whether the groundwater is polluted using fluorescence parameters of organic matters, contents of organic matters and UV parameters which have been reported at home and abroad.

These parameters includes the following:
(1) five fluorescent components (specifically see FIG. 4) and relative contents thereof (C1, C2, C3, C4 and C5) obtained from Parallel Factor Analysis on the three-dimensional fluorescence spectra of 43 samples (not including leachate samples) provided by Embodiment one;
(2) a ratio HIX of a fluorescence integral area within a band range of 435 nm to 480 nm in the emission spectrum to a fluorescence integral area within a band range of 300 nm to 345 nm under the sample excitation wavelength of 245 nm;
(3) a ratio β:α of a maximum fluorescence intensity $I_3$ at the excitation wavelength of 310 nm within the emission wavelength range of 420 nm to 435 nm to a fluorescence intensity a at the excitation wavelength of 310 nm and the emission wavelength of 380 nm;
(4) a ratio BIX of a fluorescence intensity at the excitation wavelength of 310 nm and the emission wavelength of 380 nm to a fluorescence intensity at the excitation wavelength of 310 nm and the emission wavelength of 430 nm;
(5) contents of organic matters (DOC); and
(6) absorbance a(355) of organic matters at 355 nm.

The detection results are shown in Table 7.

TABLE 7

| | C1 | C2 | C3 | C4 | C5 | HIX | β:α | BIX | DOC | a(355) |
|---|---|---|---|---|---|---|---|---|---|---|
| A-b | 71.74 | 39.24 | 61.09 | 36.14 | 90.67 | 1.83 | 1.02 | 1.08 | 2.09 | 0.17 |
| A-j1 | 63.62 | 28.03 | 221.82 | 6.92 | 295.19 | 0.73 | 1.07 | 1.17 | 1.85 | 0.07 |
| A-j2 | 69.46 | 30.94 | 82.77 | 37.81 | 130.99 | 1.23 | 1.15 | 1.28 | 1.84 | 0.06 |
| A-k1 | 65.97 | 32.36 | 76.95 | 36.49 | 114.15 | 1.48 | 1.08 | 1.25 | 1.71 | 0.19 |
| A-k2 | 65.46 | 32.58 | 117.15 | 29.40 | 163.75 | 1.19 | 1.13 | 1.16 | 1.53 | 0.08 |
| B-b | 69.38 | 44.32 | 199.47 | 37.79 | 138.80 | 0.84 | 0.79 | 0.88 | 2.30 | 0.60 |
| B-j1 | 69.29 | 44.43 | 193.15 | 32.42 | 136.34 | 0.87 | 1.07 | 1.15 | 2.41 | 0.49 |
| B-j2 | 72.56 | 46.28 | 167.08 | 36.81 | 121.05 | 1.06 | 1.05 | 1.09 | 3.08 | 0.24 |
| B-k1 | 74.02 | 47.54 | 172.55 | 40.68 | 119.85 | 0.99 | 1.08 | 1.17 | 2.88 | 0.54 |
| B-k2 | 75.53 | 43.34 | 175.30 | 36.20 | 121.81 | 0.94 | 1.10 | 1.20 | 2.22 | 0.92 |
| C-b | 54.64 | 48.08 | 86.39 | 25.78 | 135.62 | 1.20 | 0.94 | 1.00 | 1.97 | 0.91 |
| C-j1 | 183.32 | 145.44 | 132.83 | 80.33 | 256.11 | 2.41 | 0.92 | 0.95 | 2.88 | 5.20 |
| C-j2 | 82.19 | 63.37 | 106.87 | 35.42 | 181.84 | 1.38 | 0.98 | 1.02 | 2.84 | 1.13 |
| D-b | 183.84 | 96.43 | 208.61 | 71.92 | 68.45 | 1.67 | 1.11 | 1.26 | 0.18 | 1.67 |
| D-j | 455.10 | 406.85 | 181.68 | 180.41 | 392.63 | 4.25 | 0.81 | 0.85 | 4.54 | 5.20 |
| D-k | 192.38 | 103.22 | 198.75 | 79.88 | 77.91 | 1.81 | 1.06 | 1.19 | 2.65 | 1.31 |
| E-b | 148.82 | 87.74 | 69.50 | 70.94 | 106.34 | 2.82 | 0.98 | 1.06 | 1.99 | 0.39 |
| E-j | 363.42 | 336.95 | 90.38 | 132.31 | 208.98 | 5.68 | 0.79 | 0.83 | 2.78 | 3.65 |
| E-k1 | 309.35 | 238.35 | 130.84 | 105.72 | 21.16 | 4.50 | 0.85 | 0.92 | 2.64 | 2.11 |
| E-k2 | 221.15 | 168.95 | 100.62 | 82.01 | 0.00 | 5.19 | 1.15 | 0.90 | 3.25 | 3.91 |
| F-b | 145.64 | 91.24 | 189.55 | 60.15 | 113.67 | 1.73 | 0.99 | 1.12 | 5.14 | 17.16 |

TABLE 7-continued

|     | C1      | C2      | C3      | C4      | C5     | HIX  | β:α  | BIX  | DOC   | a(355) |
|-----|---------|---------|---------|---------|--------|------|------|------|-------|--------|
| F-j | 1024.70 | 910.93  | 690.95  | 38.94   | 476.86 | 3.56 | 0.82 | 0.86 | 3.16  | 1.73   |
| G-b | 628.17  | 355.26  | 304.22  | 243.12  | 327.81 | 3.39 | 1.03 | 1.12 | 4.98  | 2.16   |
| G-j1 | 595.00 | 691.76  | 451.66  | 0.00    | 343.43 | 3.43 | 0.84 | 0.84 | 5.90  | 7.72   |
| G-j2 | 1054.57 | 629.55 | 568.15  | 363.63  | 483.07 | 3.60 | 0.97 | 1.05 | 6.08  | 3.71   |
| G-k | 676.39  | 370.21  | 309.88  | 234.13  | 344.94 | 3.50 | 1.07 | 1.20 | 5.13  | 2.32   |
| H-b | 564.47  | 373.57  | 304.49  | 219.23  | 279.43 | 3.63 | 0.96 | 1.04 | 5.47  | 4.27   |
| H-j1 | 572.66 | 382.19  | 298.86  | 213.32  | 338.35 | 3.58 | 0.95 | 1.01 | 5.17  | 4.13   |
| H-j2 | 566.19 | 374.72  | 299.83  | 212.59  | 339.85 | 1.23 | 0.93 | 1.00 | 5.02  | 4.11   |
| H-k1 | 567.46 | 376.72  | 307.12  | 208.90  | 305.51 | 3.54 | 0.94 | 1.03 | 5.33  | 4.38   |
| H-k2 | 564.87 | 375.63  | 314.49  | 199.96  | 273.01 | 0.73 | 0.94 | 1.01 | 5.58  | 4.26   |
| I-j1 | 184.67 | 151.19  | 113.16  | 102.31  | 204.32 | 3.28 | 0.89 | 0.94 | 2.25  | 2.55   |
| I-j2 | 56.18  | 73.49   | 94.98   | 357.43  | 170.47 | 5.57 | 0.83 | 0.90 | 2.26  | 1.08   |
| J-j1 | 3660.10 | 2392.66 | 3887.60 | 4457.70 | 0.00 | 4.73 | 1.01 | 1.04 | 11.07 | 14.77  |
| J-j2 | 1046.44 | 717.80 | 721.69  | 2252.23 | 870.87 | 6.76 | 0.94 | 0.96 | 4.68  | 2.80   |
| K-b | 110.20  | 71.48   | 206.45  | 31.77   | 138.70 | 1.14 | 1.05 | 1.22 | 2.06  | 1.11   |
| K-j1 | 649.68 | 542.04  | 585.51  | 2185.42 | 230.18 | 8.43 | 0.89 | 0.94 | 4.43  | 2.84   |
| K-j2 | 897.32 | 781.00  | 527.18  | 19.61   | 0.00   | 4.22 | 0.83 | 0.87 | 9.77  | 13.42  |
| K-k | 333.30  | 244.93  | 200.09  | 220.86  | 160.32 | 3.97 | 0.92 | 0.97 | 4.20  | 1.87   |
| L-b | 145.22  | 107.51  | 77.80   | 51.67   | 0.00   | 3.67 | 0.93 | 0.97 | 2.19  | 0.68   |
| L-j | 754.77  | 560.55  | 1754.77 | 3727.47 | 163.96 | 3.07 | 0.92 | 0.98 | 3.31  | 0.70   |
| L-k1 | 437.36 | 350.85  | 170.86  | 144.67  | 0.00   | 5.65 | 0.83 | 0.90 | 2.48  | 1.40   |
| L-k2 | 143.40 | 106.63  | 63.14   | 50.84   | 0.00   | 4.12 | 0.89 | 0.94 | 2.15  | 1.33   |

Table 7 illustrates values of ten parameters of 43 groundwater samples. The principal component analysis was carried out by means of the Statistical Package for the Social Sciences (SPSS) software, and Table 8 and Table 9 were obtained. The 10 sets of spectra and concentration parameters can be classified into three categories, that is, principal components PC1, PC2 and PC3.

TABLE 8

| Parameter | PC1   | PC2    | PC3    |
|-----------|-------|--------|--------|
| C3        | 0.953 |        | 0.136  |
| C1        | 0.914 | 0.149  | 0.312  |
| C2        | 0.881 | 0.254  | 0.330  |
| C4        | 0.880 |        |        |
| BIX       |       | -0.939 | -0.141 |
| β:α       |       | -0.924 |        |
| HIX       | 0.389 | 0.695  |        |
| a(355)    | 0.313 | 0.174  | 0.839  |
| DOC       | 0.531 | 0.206  | 0.729  |
| C5        | 0.429 | 0.396  | -0.526 |

Figure 4:
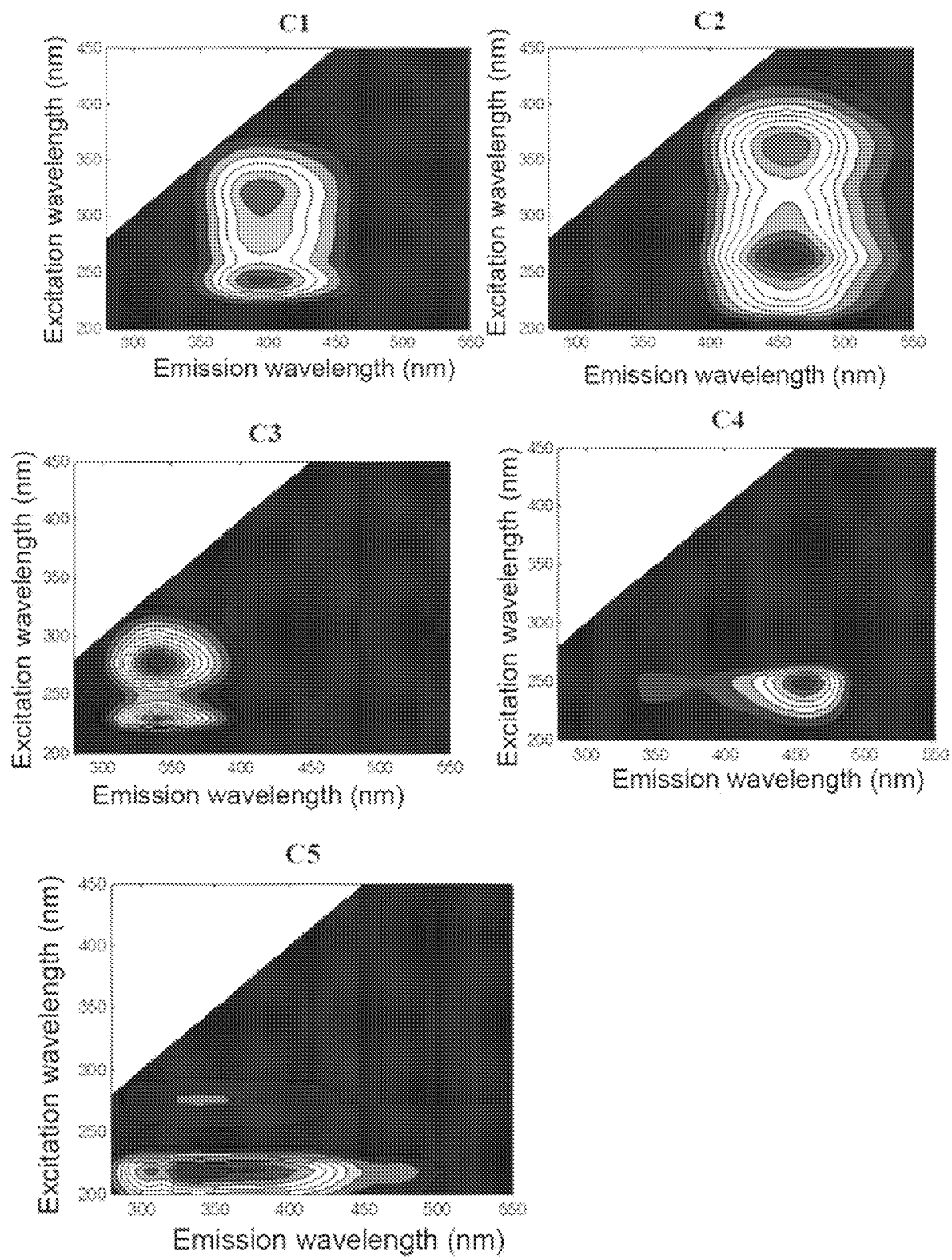
FIG. 4 illustrates three-dimensional fluorescence spectrums of five fluorescent components obtained from Parallel Factor Analysis of 43 groundwater samples in Comparative example one.

As can be seen from Table 8, C1, C2, C3 and C4 have higher scores on PC1, and in combination with the three-dimensional fluorescence spectrums in FIG. 4, it can be seen that components C1, C2 and C4 are humic-like substances. Therefore, the first classification PC1 represents the content of humic-like substances in the groundwater. The absolute values of parameters HIX, BIX and β:α have higher scores on PC2. PC2 represents the humification level of organic matters in the groundwater, since HIX represents humification and BIX and β:α are opposite to humification with negative scores on PC2, DOC and a(355) have higher scores on PC3, and both parameters are related to the total content of organic matters, that is, PC3 represents the total content of organic matters in the groundwater.

Table 9

| Sample | PC1       | PC2       | PC3       |
|--------|-----------|-----------|-----------|
| A-b    | -0.520708 | -0.537181 | -0.359909 |
| A-j1   | -0.20649  | -1.10124  | -0.77453  |
| A-j2   | -0.15806  | -1.77868  | -0.5881   |
| A-k1   | -0.28084  | -1.37279  | -0.54716  |

Table 9-continued

| Sample | PC1      | PC2      | PC3      |
|--------|----------|----------|----------|
| A-k2   | -0.2665  | -1.29983 | -0.6404  |
| B-b    | -0.92169 | 0.897594 | -0.14585 |
| B-j1   | -0.33531 | -1.09683 | -0.33779 |
| B-j2   | -0.42015 | -0.79759 | -0.19276 |
| B-k1   | -0.31309 | -1.19007 | -0.23008 |
| B-k2   | -0.27483 | -1.37478 | -0.32434 |
| C-b    | -0.68678 | -0.02378 | -0.2634  |
| C-j1   | -0.57889 | 0.457296 | 0.255496 |
| C-j2   | -0.54973 | -0.20002 | -0.17658 |
| D-b    | -0.16094 | -1.55168 | -0.59193 |
| D-j    | -0.35664 | 1.534633 | 0.33964  |
| D-k    | -0.24515 | -1.09247 | -0.14453 |
| E-b    | -0.4848  | -0.16849 | -0.40893 |
| E-j    | -0.59792 | 1.802704 | 0.037482 |
| E-k1   | -0.64173 | 0.990281 | 0.112965 |
| E-k2   | -0.42421 | -0.03155 | 0.388512 |
| F-b    | -0.69006 | -0.5118  | 2.490542 |
| F-j    | 0.403848 | 1.285538 | -0.44553 |
| G-b    | 0.263817 | -0.42988 | -0.03737 |
| G-j1   | -0.17206 | 1.277288 | 1.113753 |
| G-j2   | 0.669454 | 0.081633 | 0.168438 |
| G-k    | 0.427297 | -0.82844 | -0.0643  |
| H-b    | 0.017518 | 0.134528 | 0.470635 |
| H-j1   | 0.021513 | 0.296284 | 0.31711  |
| H-j2   | -0.08512 | 0.066255 | 0.430458 |
| H-k1   | -0.00165 | 0.248055 | 0.432107 |
| H-k2   | -0.12258 | -0.11459 | 0.693741 |
| I-j1   | -0.58858 | 0.699386 | -0.17747 |
| I-j2   | -0.64713 | 1.375604 | -0.47716 |
| J-j1   | 4.70689  | -1.05004 | 2.679699 |
| J-j2   | 1.588016 | 1.007261 | -1.33788 |
| K-b    | -0.26147 | -1.20885 | -0.3619  |
| K-j1   | 0.775845 | 1.223841 | -0.39026 |
| K-j2   | -0.2628  | 1.141529 | 3.175629 |
| K-k    | -0.33302 | 0.529429 | 0.106144 |
| L-b    | -0.68073 | 0.393431 | -0.1412  |
| L-j    | 1.685438 | -0.13538 | -0.89109 |
| L-k1   | 2.474007 | 1.732408 | -3.10196 |
| L-k2   | -0.76399 | 0.720979 | -0.05995 |

As can be seen from Table 9, for the polluted groundwater and unpolluted groundwater, in PC1, the only difference between them is that the scores are positive or negative, and there is no significant difference between polluted groundwater samples F-j, J-j1, J-j2, K-j1 and L-j and unpolluted groundwater samples in PC1, that is, whether the groundwater is polluted cannot be determined according to humic content parameters C1, C2, C3 and C4; for PC2, polluted groundwater samples F-j, J-j1, J-j2, K-j1, L-j cannot be distinguished from other unpolluted groundwater samples, that is, whether the groundwater is polluted cannot be determined according to humification parameters HIX, BIX and β:α; for PC3, the polluted groundwater samples F-j, J-j1, J-j2, K-j1 and L-j cannot be distinguished from other unpolluted groundwater samples through numerical scores, that is, whether the groundwater is polluted cannot be determine according to the organic matter content parameters DOC and a(355).

Therefore, whether the groundwater is polluted by the leachate cannot be determined according to the above ten indexes.

It can be seen from comparison between the embodiments and comparative examples that only the detection method provided by the present invention can achieve the rapid detection for the condition of landfill leachate polluting groundwater.

The applicant has stated that although the compound, the rapid detection method for a condition of landfill leachate polluting groundwater and the application thereof provided by the present invention are described through the embodiments described above, the present invention is not limited to the processes and steps described above, which means that implementation of the present invention does not necessarily depend on the processes and steps described above. It should be apparent to those skilled in the art that any improvements made to the present invention, equivalent replacements of raw materials selected in the present invention and addition of adjuvant ingredients thereof, and selections of specific methods, etc., all fall within the protection scope and the disclosed scope of the present invention.

What is claimed is:

1. A rapid detection method for a condition of landfill leachate polluting groundwater, the method comprising:
   carrying out fluorescence detection on groundwater in a specific region of a landfill, and
   determining whether the groundwater is polluted according to a ratio of fluorescence intensities at specific excitation/emission (Ex/Em) wavelengths in a specific fluorescence region, wherein
   water samples from a site background monitoring well, a pollution monitoring well, and a pollution diffusion monitoring well of the landfill are detected respectively, and whether the groundwater is polluted is determined according to the ratio of fluorescence intensities of the water sample in different specific fluorescence regions in the pollution monitoring well or the pollution diffusion monitoring well or whether the groundwater is polluted is determined according to the ratio of fluorescence intensities at the specific Ex/Em wavelengths in the specific fluorescence region among the site background monitoring well, the pollution monitoring well, or the pollution diffusion monitoring well,
   the specific fluorescence region comprises a region where the Ex/Em is at 240-260 nm/450 nm, and further comprises a region where the Ex/Em is at 215-225 nm/335-345 nm and 240-260 nm/410 nm,
   in water sample detection of the pollution monitoring well, if $I_{240-260/450}/I_{240-260/410} \geq 1$, the groundwater is considered to be polluted,
   in water sample detection of the pollution diffusion monitoring well, if $I_{240-260/450}/I_{240-260/410} \geq 1$, the groundwater is considered to be polluted, and
   the rapid detection method achieves rapid detection on whether landfill leachate pollutes groundwater using a portable fluorescence detector on site.

2. The rapid detection method of claim 1, wherein if a ratio of a fluorescence intensity $I_{240-260/450}$ of the pollution monitoring well at 240-260 nm/450 nm to a fluorescence intensity $I_{240-260/450}$ of the site background monitoring well at 240-260 nm/450 nm is greater than 6.8, the groundwater is considered to be polluted.

3. The rapid detection method of claim 2, wherein if the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is less than 4, the groundwater is considered to be not polluted.

4. The rapid detection method of claim 3, wherein if the ratio of the fluorescence intensity $I_{240-260/450}$ of the pollution monitoring well at 240-260 nm/450 nm to the fluorescence intensity $I_{240-260/450}$ of the site background monitoring well at 240-260 nm/450 nm is 4 to 6.8, the ratio of fluorescence intensities of the water samples of the site background monitoring well, the pollution monitoring well and the pollution diffusion monitoring well in different specific fluorescence regions is further measured in order to determine whether the groundwater is polluted.

5. The rapid detection method of claim 1, wherein if a ratio $I_a$ of a fluorescence intensity $I_{215-225/335-345}$ at 215-225 nm/335-345 nm to a fluorescence intensity $I_{240-260/410}$ at 240-260 nm/410 nm of the site background monitoring well, a ratio $I_b$ of a fluorescence intensity $I_{215-225/335-345}$ at 215-225 nm/335-345 nm to a fluorescence intensity $I_{240-260/410}$ at 240-260 nm/410 nm of the pollution monitoring well, and a ratio $I_c$ of a fluorescence intensity $I_{215-225/335-345}$ at 215-225 nm/335-345 nm to a fluorescence intensity $I_{240-260/410}$ at 240-260 nm/410 nm of the pollution diffusion monitoring well are all greater than 1 or all less than 1, the groundwater is considered to be not polluted.

6. The rapid detection method of claim 5, wherein if the $I_a$, $I_b$ and $I_c$ are not all greater than 1 or not all less than 1, the groundwater is considered to be polluted.

7. The rapid detection method of claim 5, wherein if a ratio of the fluorescence intensity $I_{240-260/410}$ of the pollution monitoring well at 240-260 nm/410 nm to the fluorescence intensity $I_{240-260/410}$ at 240-260 nm/410 nm of the site background monitoring well is greater than 6.8, the groundwater is considered to be polluted.

8. The rapid detection method of claim 7, wherein if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is less than 4, the groundwater is considered to be not polluted.

9. The rapid detection method of claim 7, wherein if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is 4 to 6.8, and the $I_a$, $I_b$ and $I_c$ are all greater than 1 or all less than 1, the groundwater is considered to be not polluted.

10. The rapid detection method of claim 9, wherein if the ratio of the fluorescence intensity $I_{240-260/410}$ of the pollution monitoring well at 240-260 nm/410 nm to the fluorescence intensity $I_{240-260/410}$ of the site background monitoring well at 240-260 nm/410 nm is 4 to 6.8, and the $I_a$, $I_b$ and $I_c$ are not all greater than 1 or not all less than 1, the groundwater is considered to be polluted.

* * * * *